United States Patent
Lightner et al.

(10) Patent No.: US 11,419,316 B2
(45) Date of Patent: Aug. 23, 2022

(54) HYBRID DAIRY CATTLE AND SYSTEMS FOR MAXIMIZING HYBRID ADVANTAGE

(71) Applicant: ABS Global, Inc., DeForest, WI (US)

(72) Inventors: Jon Lightner, DeForest, WI (US); Richard Williams, DeForest, WI (US)

(73) Assignee: ABS Global, Inc., DeForest, WI (US)

( * ) Notice: Subject to any disclaimer, the term of this patent is extended or adjusted under 35 U.S.C. 154(b) by 801 days.

(21) Appl. No.: 16/189,603

(22) Filed: Nov. 13, 2018

(65) Prior Publication Data

US 2019/0075768 A1 Mar. 14, 2019

Related U.S. Application Data

(60) Division of application No. 15/169,459, filed on May 31, 2016, now Pat. No. 10,159,226, which is a continuation of application No. PCT/US2015/060576, filed on Nov. 13, 2015.

(60) Provisional application No. 62/106,151, filed on Jan. 21, 2015, provisional application No. 62/080,145, filed on Nov. 14, 2014.

(51) Int. Cl.
| | | |
|---|---|---|
| A01K 67/027 | (2006.01) | |
| A61D 19/02 | (2006.01) | |
| A61K 35/52 | (2015.01) | |
| A61K 35/54 | (2015.01) | |
| A61D 19/00 | (2006.01) | |
| C12N 5/12 | (2006.01) | |
| C12N 5/26 | (2006.01) | |
| C12N 5/073 | (2010.01) | |
| A01K 67/02 | (2006.01) | |
| A61D 19/04 | (2006.01) | |

(52) U.S. Cl.
CPC .......... *A01K 67/027* (2013.01); *A01K 67/02* (2013.01); *A61D 19/00* (2013.01); *A61D 19/02* (2013.01); *A61D 19/04* (2013.01); *A61K 35/52* (2013.01); *A61K 35/54* (2013.01); *C12N 5/0604* (2013.01); *C12N 5/12* (2013.01); *C12N 5/166* (2013.01); *A01K 2227/101* (2013.01)

(58) Field of Classification Search
None
See application file for complete search history.

(56) References Cited

FOREIGN PATENT DOCUMENTS

| | | |
|---|---|---|
| RU | 2490887 C1 | 8/2013 |
| WO | WO 03/096799 A2 | 11/2003 |
| WO | WO 2009/063512 A1 | 5/2009 |
| WO | WO 2010/068999 A1 | 6/2010 |
| WO | WO 2016/077693 A1 | 5/2016 |

OTHER PUBLICATIONS

Cook, "A Comparison of Daughters of Sires in Artificial Breeding at Different Levels of management," A Thesis submitted in partial fulfillment of the requirements for the degree of Master of Science in Diary Husbandry, Utah State University (1960) retrieved from the Internet: https://digitalcommons.usu.edu/cgi/viewcontent.cgi?article=3747&context=etd.
Extended European Search Report issued in European Appln. 19158577.7 dated May 10, 2019.
Lon McGilliard et al., "Predicting daughter milk production from dam index," A Dissertation Submitted to the Graduate Faculty in Partial Fulfillment of the Requirements for the Degree of Doctor of Philosophy, Iowa Statement University (1974) retrieved from the Internet: https://lib.dr.iastate.edu/cgi/viewcontent.cgi?article=7354&context=rtd (2019).
Fischer et al., "Estimates of Heterosis for In Vitro Embryo Production Using Reciprocal Crosses in Cattle," *Theriogenology*, 54:1433-1442 (2000).
Hansen., L., "Dairy Extension. Crossbreeding in Dairy Cattle Requires the Use of THREE Breeds," Dairy Star, University of Minnesota, 2 pages, Nov. 11, 2006, http://www.extension.umn.edu/agriculture/dairy/reproduction-and-genetics/crossbreeding-requires-three-breeds, retrieved Sep. 21, 2017.
Hansen, P., "Dairy Reproduction Notes", University of Florida, Farms.com No. 2, (Jul. 3, 2005), 2 pages.
Hansen, P.J., Current Status and Applications of New Embryo Technologies in Dairy Herd Management, WCDS Advances in Dairy Technology, 19:217-226 (2007).
Hansen, P.J., "Realizing the promise of IVF in cattle—an overview," *Theriogenology*, 65:119-125 (2006).
Hazel et al., "Production, fertility, survival, and body measurements of Montebéliarde-sired crossbreds compared with pure Holsteins during their first 5 lactations," *J. Dairy Sci.*, 97:2512-2525 (2014).
International Search Report dated Feb. 25, 2016, in International Patent Application No. PCT/US2015/060576, 5 pages.
Khongdee et al., "The effect of modified roofing on the milk yield and reproductive performance of heat-stressed dairy cows under hot-humid conditions," *Animal Science Journal*, 81:606-611 (2010).
Kosgey et al., "Evaluation of Closed Adult Nucleus Multiple Ovulation and Embryo Transfer and Conventional Progeny Testing Breeding Schemes for Milk Production in Tropical Crossbred Cattle," *J. Dairy Sci.*, 88:1582-1594 (2005).
Madalena et al., "Dairy cattle genetics and its applications in Brazil," Livestock Research for Rural Development, pp. 24-30 (2012), available at http://www.Irrd.org/Irrd24/6/made24097.htm, retrieved Jan. 25, 2016.
Madalena, F.E., "Dairy cattle breeding programme in Brazil development of the Brazilian milking hybrid (MLB)," Proceedings of Workshop on Developing Breeding Strategies for Lower Input Animal Production Environments, pp. 365-378(2000).
Madalena, et al., Evaluation of Strategies for Crossbreeding of Dairy Cattle in Brazil, *Journal of Dairy Science*, 73(2):1887-1901 (1990).

(Continued)

*Primary Examiner* — Marcia S Noble
(74) *Attorney, Agent, or Firm* — Foley & Lardner LLP

(57) ABSTRACT

Systems for selecting, generating, and breeding hybrid dairy cattle are described, as are methods for maintaining herds of hybrid cattle.

20 Claims, 6 Drawing Sheets

(56) References Cited

OTHER PUBLICATIONS

Quarles & Brady LLP correspondence, Re: U.S. Appl. No. 15/169,459—Lightner, et al., (filed Oct. 10, 2017), 4 pages.
Risstrom, I., "Herd recording. Smallholder dairying in the tropics." Nairobi, Kenya (1999), available at https://www.ilri.org/InfoServ/Webpub/fulldocs/SmHDairy/chap14.html, retrieved Jan. 25, 2016.
Rutledge, J.J., Technology innovations to enhance livestock agribusiness, Babcock Institute for International Dairy Research and Development, University of Wisconsin—Madison, Wartazoa, Indonesian Bulletin of Animal and Veterinary Sciences, 14(2):58-60 (2004).
Schefers et al., "Genomic selection in dairy cattle: Integration of DNA testing into breeding programs," *Animal Front*, 2(1):4-9 (2012).
Swan et al., "Evaluation and Exploitation of Crossbreeding in Dairy Cattle," *Journal of Dairy Science*, 75(2):624-639 (1992).
Written Opinion completed Feb. 25, 2016, in International Patent Application No. PCT/US2015/060576, 8 pages.
Xue et al., "Milk production and energy efficiency of Holstein and Jersey-Holstein crossbred dairy cows offered diets containing grass silage," *J. Dairy Sci.*, 94(3):1455-1464 (2011).
Examination Report on EP 19158577.7 dated May 3, 2021 (5 pages).
Madalena et al., Dairy cattle genetics and its applications in Brazil; Live stock Research for Rural Development, vol. 6, No. 24, pp. 1-25, Jun. 1, 2012.
Journal of livestock medicine, 1995, n.389, p. 41-49 (machine translation).
LIAJ News, 2012, No. 135, p. 3-6 (machine translation).
Sel'Skokhozyajstvennaya Bioloogiya, 1981, vol. 16, No. 5, p. 661-664 (machine translation).
Zi et al., "Development of embryos after in vitro fertilization of bovine oocytes with sperm from either yaks (*Bos grunniens*) or cattle (*Bos taurus*)", Animal Reproduction Science, 2008, vol. 108, pp. 208-215.

HYBRID DAIRY CATTLE AND SYSTEMS FOR MAXIMIZING HYBRID ADVANTAGE

CROSS-REFERENCE TO RELATED APPLICATIONS

This application is a divisional of U.S. patent application Ser. No. 15/169,459, filed Nov. 13, 2015, which is continuation of International Patent Application No. PCT/US15/60576, filed Nov. 13, 2015, which claims the benefit of U.S. Provisional Application No. 62/106,151, filed Jan. 21, 2015, and U.S. Provisional Application No. 62/080,145, filed Nov. 14, 2014, of which each are incorporated herein by reference in their entirety.

BACKGROUND

The bovine industry is highly specialized and dairy cattle have been bred to efficiently produce large volumes of milk. The United States dairy herd produced 83.9 billion kg (185 billion lbs.) of milk in 2007, up from 52.6 billion kg (116 billion lbs.) in 1950, yet there are only about 9 million cows on U.S. dairy farms—about 13 million fewer than in 1950.

SUMMARY

The present invention provides technologies for generating and/or maintaining a herd of high-quality hybrid (i.e., cross-bred) dairy cattle. The present invention also provides technologies for identification, characterization, and/or selection of dairy cattle breeding stock sires/sire lines and dams/dam lines.

Among other things, the present invention encompasses the identification of a source of a problem with traditional cross-breeding technologies, particularly those that select one or both of the sire/sire line or dam/dam line (referred to herein as male and female "F0 individuals" or "F0 lines") based on performance characteristics of the F0 individuals or lines themselves. For example, it is particularly common in the field of dairy cattle breeding to select dams/dam lines based on the milk-production characteristics of particular dam individuals or dam lines. The present disclosure encompasses the recognition that such approaches may actually fail to select F0 individuals or lines that are most desirable for creating hybrid dairy animals.

Moreover, the present invention encompasses the recognition that, while cross breeds display hybrid vigor and idealized traits based upon genetic selection, it is difficult using presently available strategies to maintain and reproduce such traits among subsequent generations within the herd.

In some embodiments, the invention provides methods comprising steps of: assaying members of each of a plurality of F1 crossbreed cattle; and selecting as breeding stock F0 cattle based on the performance of the F1 crossbreed cattle.

In some embodiments, selecting F0 cattle based on performance comprises selecting based on level or nature of at least one performance characteristics for which the F1 cattle are superior to both F0s. In some embodiments, the step of selecting cattle based on performance comprises detecting a genetic signature correlated with the level or nature of the one or more performance characteristics.

In some embodiments, the F1 cattle are dairy cattle. In some embodiments, the F1 cattle are dairy cattle females. In some embodiments, the F1 cattle are beef-on-dairy cattle.

In some embodiments, the invention provides methods of breeding cattle comprising: generating an embryo from male and female F0 gametes, wherein one or both of the male and female F0 gametes is from an F0 individual selected based on performance of prior F1 progeny resulting from a cross of gametes from the F0 individual, wherein the male and female F0 gametes are from different breeds.

In some embodiments, the invention provides methods of generating an F1 herd of animals comprising steps of: implanting into each of a plurality of host female cattle, an F1 embryo resulting from fertilization of an F0 female gamete with an F0 male gamete, wherein one or both of the male and female F0 gametes is from an F0 individual selected based on performance of prior F1 individuals resulting from a cross of gametes from the F0 individual.

In some embodiments, the invention provides methods of maintaining an F1 crossbreed herd of animals comprising steps of: implanting an F1 crossbreed embryo into each of a plurality of F1 female dairy cattle, wherein each of the F1 female dairy cattle resulted from a first "F1-selected crossbreed cross", wherein an "F1-selected cross" is one that involves fertilization of an F0 female gamete with an F0 male gamete, wherein: a) the F0 male and female gametes are from different breeds; and b) one or both of the F0 male and female gametes is from an individual or line selected performance of prior F1 progeny generated in crosses of the same individual or line; wherein each implanted F1 crossbreed embryo results from a second F1-selected crossbreed cross.

In some embodiments, the invention provides methods of maintaining a crossbred herd of hybrid F1 animals possessing desired traits, wherein the hybrid state of the F1 trait is maintained through embryonic transfer of embryos selected based on F1 performance.

In some embodiments, the second F1-selected crossbreed cross utilizes male F0 gametes, female F0 gametes, or both male and female F0 gametes from the same individual or line utilized in the first F1-selected crossbreed cross. In some embodiments, the second F1-selected crossbreed cross utilizes male F0 gametes from the same individual or line utilized in the first F1-selected crossbreed cross. In some embodiments, the second F1-selected crossbreed cross utilizes male F0 gametes from the same individual in the first F1-selected crossbreed cross. In some embodiments, the second F1-selected crossbreed cross utilizes female F0 gametes from the same individual or line utilized in the F1-selected crossbreed cross. In some embodiments, the second F1-selected crossbreed cross utilizes female F0 gametes from the line utilized in the first F1-selected crossbreed cross.

In some embodiments, the second F1-selected crossbreed cross utilizes a male or female gamete from an individual or line different from that utilized in the first F1-selected crossbreed cross. In some embodiments, the different individual or line is selected based on improved performance of its F1 progeny relative to those of the corresponding F0 individual or line used in the first F1-progeny selected crossbreed cross.

In some embodiments, the invention provides a method further comprising steps of: assaying one or more performance characteristics of F1 individuals resulting from a plurality of crosses that utilize F0 gametes from one or both of the F0 individuals or lines utilized in the first F1-selected crossbreed cross; comparing the assayed one or more performance characteristics with those of F1 individuals resulting from a plurality of crosses that utilize F0 gametes from the different F0 individual or line, so that the different individual or line is selected as a desirable breeding stock individual or line.

In some embodiments, the invention provides herds of female cattle, each of which is pregnant with an F1 embryo resulting from fertilization of an F0 female gamete with an F0 male gamete, wherein one or both of the male and female F0 gametes is from an F0 individual selected based on performance of prior F1 individuals resulting from a cross of gametes from the F0 individual.

In some embodiments, the invention provides herds of female cattle comprising: a plurality of F1 animals, each of which was generated from F1 embryo resulting from fertilization of an F0 female gamete with an F0 male gamete, wherein one or both of the male and female F0 gametes is from an F0 individual selected based on performance of prior F1 individuals resulting from a cross of gametes from the F0 individual.

In some embodiments, the invention provides F1 herds of female cattle comprising: a plurality of F1 animals, each of which was generated from F1 embryo resulting from fertilization of an F0 female gamete with an F0 male gamete, wherein each male F0 gamete is from the same F0 individual and each female gamete is from a female within the same F0 family, wherein one or both of the F0 gametes is from an individual or family that is selected based on performance of prior F1 individuals resulting from a cross of gametes from the F0 individual or from a member of the F0 family. In some embodiments, each member of the plurality is characterized by level of one or more performance parameters that is superior to that of either F0.

In some embodiments, the invention provides pluralities of embryos, each of which was generated by fertilization of an F0 female gamete with an F0 male gamete, wherein one or both of the male and female F0 gametes is from an F0 individual selected based on performance of prior F1 individuals resulting from a cross of gametes from the F0 individual. In some embodiments, the embryos are frozen after fertilization for future implantation. In some embodiments, the embryos are generated from gametes of crossbred F0 cattle.

In some embodiments, the invention provides methods of selecting an F0 sire or sire line for use as breeding stock for dairy cattle, the method comprising steps of: assaying at least one performance attribute of at least one first F1 progeny individual that results from a first cross, which is a cross of a first candidate F0 sire individual with a particular F0 dam or dam line; comparing the assayed at least one performance attribute with that of at least one second F1 progeny individual that results from a reference cross, which reference is: a cross of a reference F0 sire individual with the particular F0 dam or dam line; or a second cross of the particular F0 sire individual with a second F0 dam or dam line, which may be the same or different from the particular F0 dam or dam line; or a cross of at least one different candidate F0 sire individual with the particular dam or dam line; and selecting as an F0 stock sire or sire line an F0 sire candidate whose at least one F1 progeny individual showed superiority in the comparing.

In some embodiments, the invention provides methods for selecting an F0 dam or dam line for use as breeding stock for dairy cattle, the method comprising steps of: assaying at least one performance attribute of at least one first F1 progeny individual that results from a first cross, which is a cross of a first candidate F0 dam or dam line with a particular F0 sire individual; comparing the assayed at least one performance attribute with that of at least one second F1 progeny individual that results from a reference cross, which reference is: a cross of a reference F0 dam or dam line with the particular F0 sire; or a second cross of the particular F0 dam or dam line with a second F0 sire, which may be the same or different from the particular F0 sire; or a cross of at least one different candidate F0 dam or dam line with the particular sire; and selecting as an F0 stock dam or dam line an F0 dam or dam line candidate whose at least one F1 progeny individual showed superiority in the comparing.

In some embodiments, pluralities of F1 progeny from each cross are assayed.

In some embodiments, potential performance attributes comprise: milk production, longevity, semen production, age at first calving, body depth, cell counts, cow conception rate, dairy form, daughter calving ease, daughter pregnancy rate, daughter still birth, fat pounds, fat percent, feet and legs score, fertility, final score, foot angle, fore udder attachment, front teat placement, heifer conception rate, ketosis, lameness rate and/or degree, locomotion, milk productive life, milking speed, protein percent, protein pounds, rear legs rear view, rear legs side view, rear teat placement, rear udder height, reproductive life, resistance to cold, resistance to disease (e.g., mastitis, metritis, etc.), rump angle, rump width, somatic cell score, sire calving ease, sire still birth, size, stature, strength, teat length, udder cleft, udder conformation, and udder depth.

In some embodiments, the invention provides methods of providing a cross-breed total performance index based on performance attributes assayed from F1 cattle. In some embodiments, a cross-breed total performance index embodied in computer-readable format. In some embodiments, the performance parameter is not shared by F0 individuals. In some embodiments, the performance parameter is superior in F1 as compared with F0 individuals or both F0 parents.

In some embodiments, crosses are repeated over time to adjust the performance characteristics of the F1 progeny.

In some embodiments, the invention provides methods of operating a business, the method comprising steps of: providing semen from a selected F0 stud for dairy cattle, which F0 stud is selected based on performance of F1 progeny resulting from prior cross-breed crosses in which semen from the selected F0 stud fertilized F0 female gametes. In some embodiments, the semen primarily includes sperm of one gender or the other. In some embodiments, semen primarily includes "female" sperm.

In some embodiments, the invention provides methods comprising steps of: collecting performance information for F1 progeny resulting from each of a plurality of crosses in which gametes from a first F0 individual are crossed with gametes from at least one second F0 individual of opposite gender from the first F0 individual; storing the performance information in a computer-readable format that permits its retrieval or analysis later in time. In some embodiments, steps of collecting performance information comprises collecting performance information for a plurality of different crosses in which gametes from the first F0 individual are crossed with gametes from a plurality of different second F0 individuals. In some embodiments, pluralities of different crosses are performed at different points in time. In some embodiments, stored performance information is compared with that from one or more crosses in which gametes from a second F0 individual of matching gender to the first F0 individual are crossed with gametes from at least one second F0 individual of the opposite gender. In some embodiments, at least one of the crosses in which gametes from the matching gender second F0 individual are crossed with gametes from at least one opposite gender second F0 individual, involved gametes from at least one opposite gender F0 individual who is the same as one with whom gametes from the first F0 individual had been crossed.

In some embodiments, the invention provides methods comprising steps of: using In Vitro Fertilization (IVF) to produce cross-breed embryos of female dairy cattle. In some embodiments, F1 cattle are crosses of F0s selected based on performance. In some embodiments, breeds for generating cross-breed embryos are selected from the following: Holstein-Friesian, Brown Swiss, Guernsey, Ayrshire, Jersey, Red & White, Milking Shorthorn, Linebackers, Dutch Belts, Burlina, Belarus Red, Belted Galloways, Canadienne, Carora, Danish Jersey, Frankeston Red, German black pied, Girolando, Illawarra, Meuse-Rhine-Issel, and Siboney de Cuba.

In some embodiments, the invention provides methods comprising steps of: breeding dairy cattle to a cross-breed index.

In some embodiments, all of the F0 female gametes are from the same F0 female individual, all of the F0 male gametes are from the same F0 male individual, or both.

In some embodiments, fertilization is performed in vitro. In some embodiments, fertilization is performed in vivo.

BRIEF DESCRIPTION OF THE DRAWING

FIG. 2A depicts representative chromosome pairs as found in somatic cells of an F1 hybrid animal resulting from a Holstein and Jersey cross. F1 hybrids are uniform: each chromosome pair has a 50/50 contribution from the two founder breed parents. Thus, the two founder breeds are represented in the same proportion in the F1 genome. Cow to cow, the two founder breeds are represented in the same proportions on each chromosome. Moreover, each individual chromosome within a chromosome pair is 100% from one founder strain. FIG. 2B illustrates representative chromosomal makeup in gametes of an F1 hybrid animal whose somatic chromosomes are depicted in FIG. 2A. As can be seen, cross-over events that occur during gamete production can result in individual chromosomes with different percentages of contributions from each of the two corresponding founder chromosomes. These cross-over events result in shuffling of encoded traits, and therefore complicate efforts to predict how and which traits are expressed in the next generation. FIGS. 2C and 2D illustrate this challenge, specifically depicting results of mating gametes of FIG. 2B with gametes of a third breed. As shown in FIG. 2C, whether from a single animal or different F1 animals, every egg will have a unique mix of haplotypes from the two breeds. On average they are uniform, but as individuals they are each unique. For example, FIG. 2D illustrates 3 different intended "replacement" individuals, who are progeny of the F1 x third breed cross illustrated in FIGS. 2A-2C and who all have overall genome contributions that are 25% founder strain 1, 25% founder strain 2, and 50% third breed but clearly have completely different genetic makeup and therefore have different traits and characteristics. This complexity increases in subsequent crosses, so that it is virtually impossible to maintain F1 hybrid traits through such conventional mating strategies.

DEFINITIONS

Figure 1:
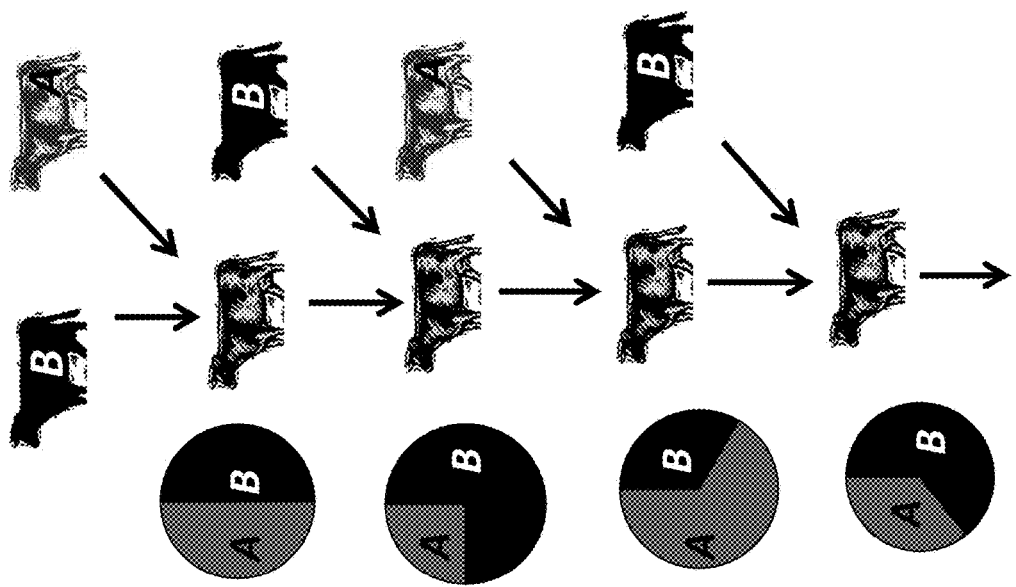
FIG. 1 depicts conventional, natural-mating cross-breeding strategies. In particular, this Figure illustrates three-breed and two-breed rotation strategies that are employed in pursuit of hybrid vigor. As can be seen with reference to this Figure, heterosis is maximum in the first cross, and neither scheme achieves this level again. Neither of the strategies depicted can generate and maintain herds of F1 animals (i.e., of 50/50 NRF/H animals). Furthermore, complications arising from crossing over and/or segregation of chromosomes can result in significant dis-uniformity in characteristics of progeny generated by the serial matings in such strategies.
Figure 1:
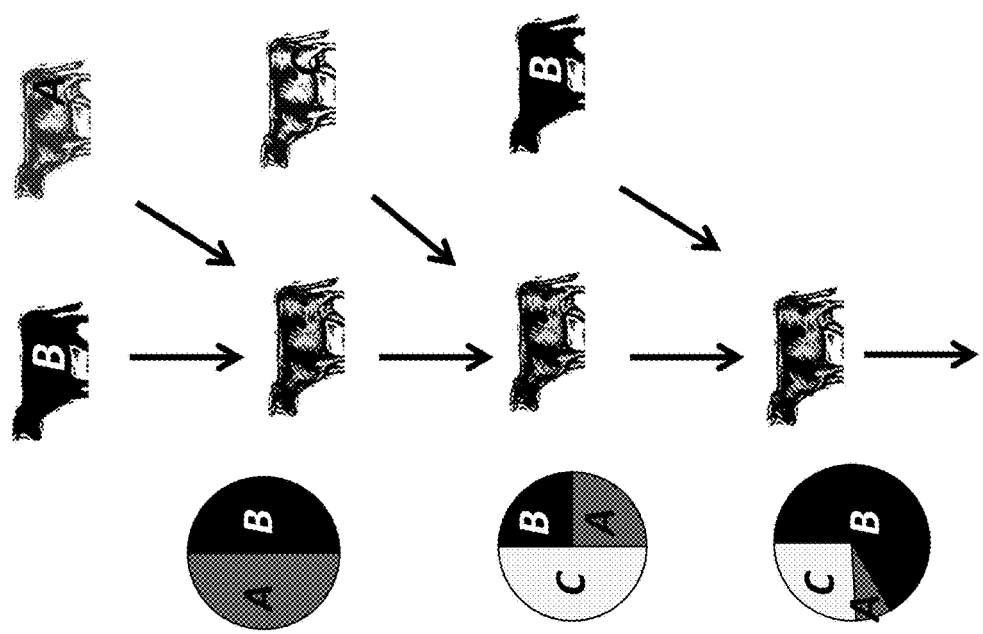
Figure 2A:
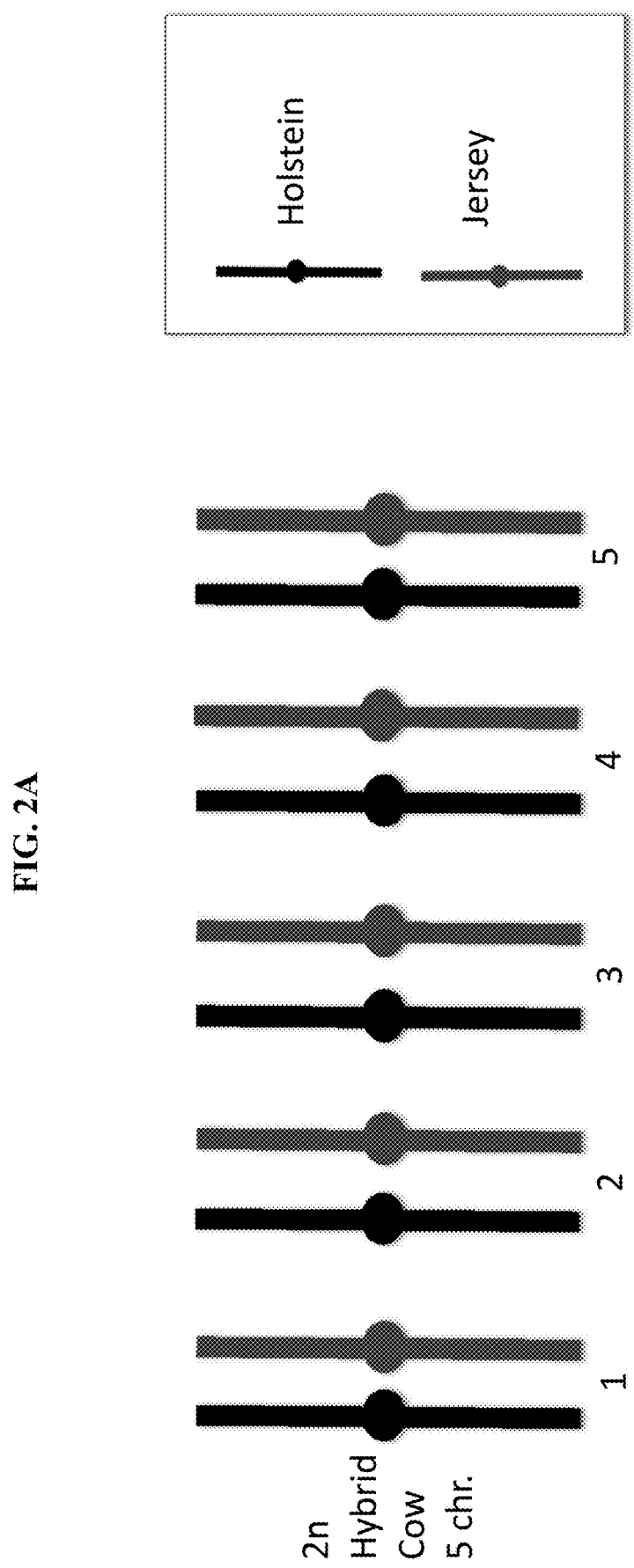
FIGS. 2A-D illustrate chromosomal segregation and crossing-over events that occur during matings as depicted in FIG. 1.
Figure 2B:
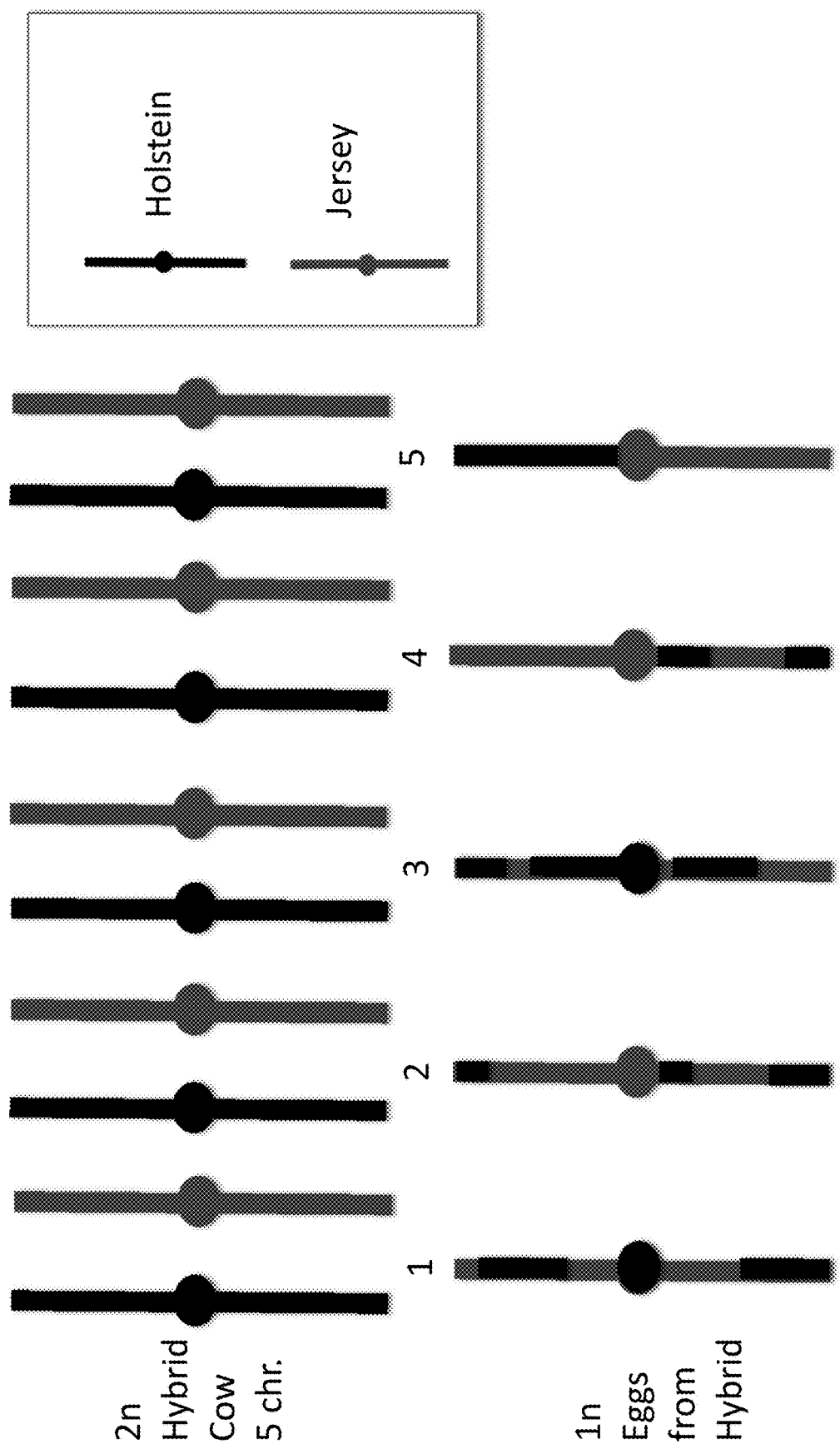
Figure 2C:
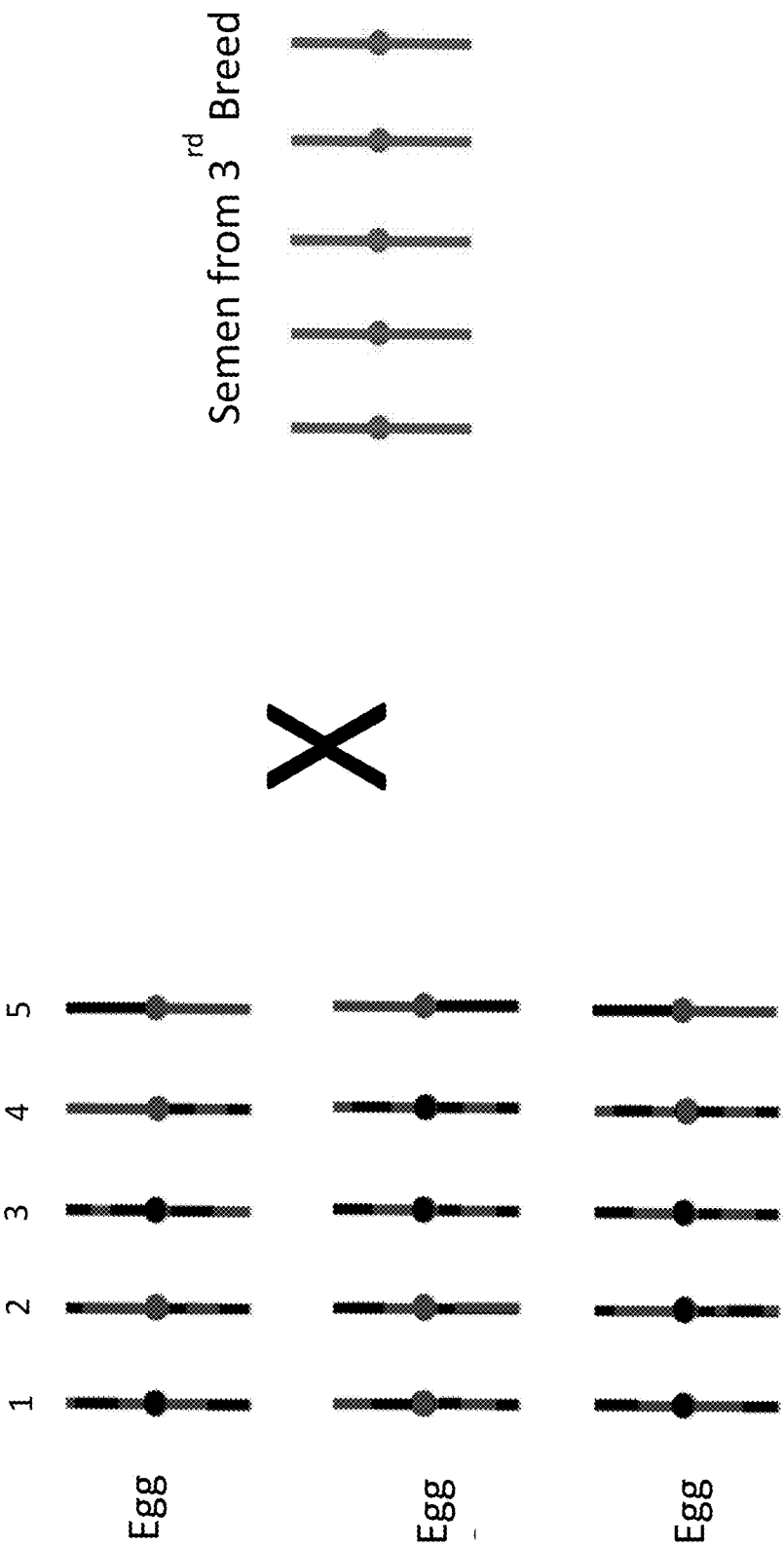
Figure 2D:
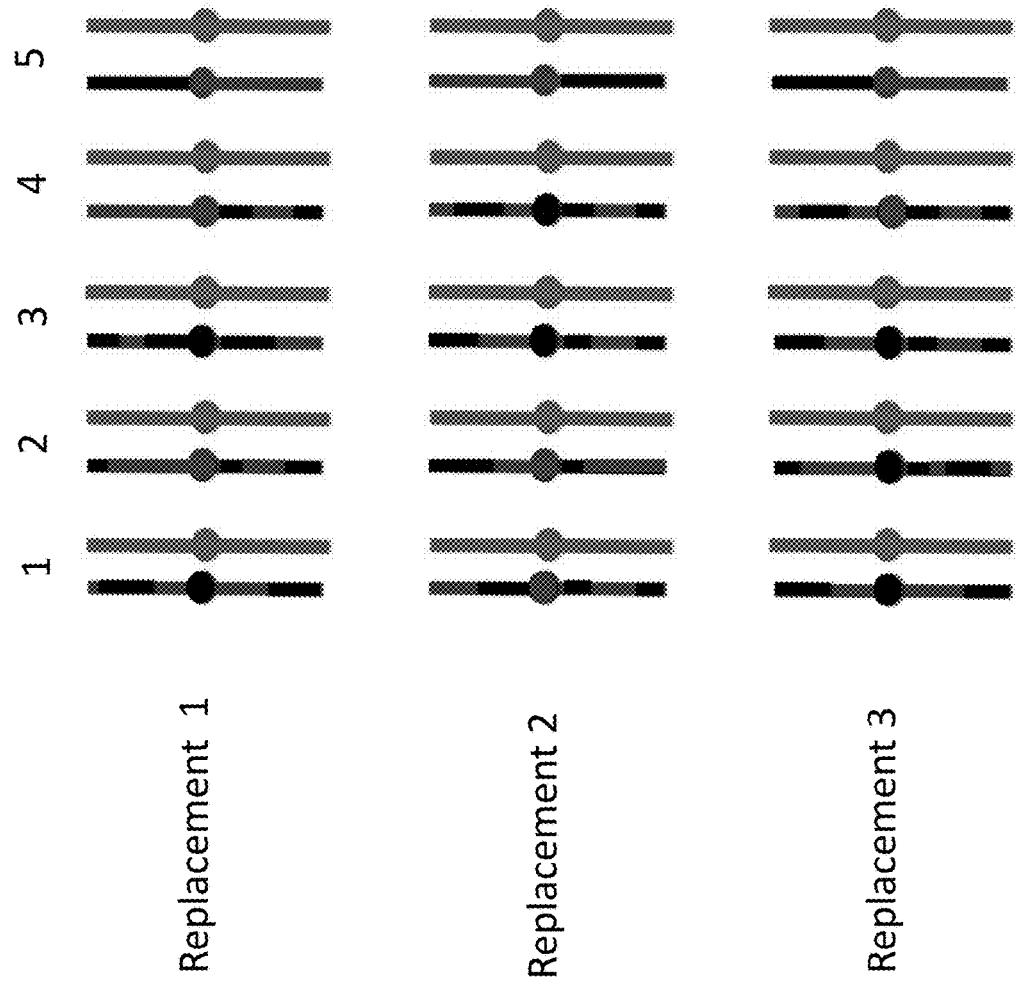

In order for the present invention to be more readily understood, certain terms are defined below. Those skilled in the art will appreciate that definitions for certain terms may be provided elsewhere in the specification, and/or will be clear from context.

Allele: As used herein, the term "allele" refers to one of two or more existing genetic variants of a specific polymorphic genomic locus.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Artificial Insemination (AI): As used herein, the term "artificial insemination (AI)" refers to introduction by the hand of man of semen into a female bovine's uterus to achieve pregnancy. In many embodiments, AI is utilized in breeding, for example so that resulting pregnancies are (or are intended to be) carried to term. In some embodiments, AI is carried out with collected semen. In some embodiments, AI is carried out with extracted semen. In some embodiments, AI is carried out with semen that has been processed; for example, in some embodiments, the semen has been sexed so that it is enriched for sperm of only one gender.

Those skilled in the art will appreciate that unless otherwise expressly indicated, the term "AI" does not encompass embryos transfer procedures, where, for example, semen may be introduced into a cow to generate embryos for transfer.

Autosome: As used herein, the term "autosome" refers to any chromosome exclusive of the X and Y sex chromosomes.

Breed: As used herein, the term "breed" refers to a group of cattle having common ancestors and/or sharing certain distinguishable traits that are not shared cattle of other breeds. Those skilled in the art are familiar with breed standards and/or characteristics. In many embodiments, a particular breed is produced and/or maintained by mating particular identified parent or parents (e.g., a particular sire with a particular dam or with any one dame from of a particular dam line) with one another.

Chromosome: As used herein, the term "chromosome" refers to a linear molecule of DNA with associated proteins in the nucleus of eukaryotic cells that carries the genes and functions in the transmission of hereditary information.

Comparable: The term "comparable" is used herein to describe two (or more) sets of conditions, circumstances, individuals, or populations that are sufficiently similar to one another to permit comparison of results obtained or phenomena observed. In some embodiments, comparable sets of conditions, circumstances, individuals, or populations are characterized by a plurality of substantially identical features and one or a small number of varied features. Those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied. Those skilled in the art will appreciate that relative language used herein (e.g., enhanced, activated, reduced, inhibited, etc.) will typically refer to comparisons made under comparable conditions.

Crossbreed: As used herein, the term "crossbreed" refers to cattle produced from gametes of individual bovines that are different breeds or varieties of cattle. Crossbreeding is often performed in dairy cattle farming to produce healthier, more productive cattle compared to the parent breeds. Crossbreeding is the deliberate mating of animals from different breeds or strains; in many embodiments crossbreeding is designed to take advantage of heterosis (hybrid vigor) for characteristics like production, fertility, and longevity. In some embodiments, the present disclosure encompasses the insight that recent developments relating to artificial insemination and/or in vitro fertilization, not typically employed in the dairy cattle industry, can be utilized to enable and/or provide certain advantages with respect to generating and/or maintaining crossbreed lines of dairy cattle as described herein. As described herein, crossbreed cattle of particular interest are hybrid cattle, in which 50% of the cattle's somatic chromosomes are from one strain or line and 50% are from a different strain or line (i.e., formed by crossing F0 individuals from first and second strains/lines that differ from one another. Those of ordinary skill in the art will appreciate, however, that the term "crossbreed" can be used in some embodiments (as is clear from context) to refer to any individual whose genome, as a result of crossing, is not 100% from any single breed. Diploid Cell: As used herein, the term "diploid cell" refers to a cell with a homologous pair of each of its autosomal chromosomes, with two copies (2n) of each autosomal genetic locus.

Embryo: As used herein, the term "embryo" refers to a fertilized oocyte (egg) prepared for immediate implantation within a female cattle or stored for eventual implantation within a female cattle.

F1: As used herein, the term "F1" refers to progeny cattle produced by crossing two F0 individuals from different breeds or lines of cattle. F1 cattle are also referred to as "hybrids," and are characterized in that 50% of their somatic chromosomes are from a first strain or line (i.e., that of one of the F0 individuals), and 50% are from a second strain or line (i.e., that of the other F0 individual), different from the first.

F0: As used herein, the term "F0" refers to parental cattle who are crossed to generate F1 hybrid cattle offspring.

Gametes: As used herein, the term "gametes" is used to refer to reproductive cells (e.g., spermatozoa or oocytes) having the haploid number of chromosomes, especially a mature sperm or egg capable of fusing with a gamete of the opposite sex to produce a fertilized egg. Gametes are produced through the process of meiosis.

Gene: As used herein, the term "gene" refers to a DNA sequence in a chromosome that codes for a product (e.g., an RNA product and/or a polypeptide product). In some embodiments, a gene includes coding sequence (i.e., sequence that encodes a particular product); in some embodiments, a gene includes non-coding sequence. In some particular embodiments, a gene may include both coding (e.g., exonic) and non-coding (e.g., intronic) sequence. In some embodiments, a gene may include one or more regulatory elements that, for example, may control or impact one or more aspects of gene expression (e.g., cell-type-specific expression, inducible expression, etc.).

Genome: As used herein, the term "genome" refers to the total genetic information carried by an individual organism or cell, represented by the complete DNA sequences of its chromosomes.

Genome Profile: As used herein, the term "genome profile" refers to a representative subset of the total information contained within a genome. Typically, a genome profile contains genotypes at a particular set of polymorphic loci. In some embodiments, a genome profile may correlate with a particular feature, trait, or set thereof characteristic of, for example, a particular animal, line, breed, or crossbreed population.

Genotype: As used herein, the term "genotype" refers to the diploid combination of alleles at a given genetic locus, or set of related loci, in a given cell or organism. A homozygous subject carries two copies of the same allele and a heterozygous subject carries two distinct alleles. In the simplest case of a locus with two alleles "A" and "a," three genotypes can be formed: A/A, A/a, and a/a.

Genotyping: As used herein, the term "genotyping" refers to an experimental, computational, or observational protocol for distinguishing an individual's genotype at one or more well-defined loci. Those skilled in the art will be aware of a variety of technologies that can usefully and effectively perform genotyping. In some embodiments, genotyping involves direct detection of a nucleic acid or nucleic acid sequence. In some embodiments, genotyping involves indirect detection of a nucleic acid or nucleic acid sequence, for example through detection or analysis of a proxy marker or event that correlates with presence of the nucleic acid or nucleic acid sequence.

Haploid Cell: As used herein, the term "haploid cell" refers to a cell with a single set (1n) chromosome of chromosomes—half the number of a somatic cell.

Heifer: As used herein, the term "heifer" refers to female cattle who have not yet produced any calves.

Hybrid: As used herein, the term "hybrid" refers to cattle produced as a result of crossing male and female gametes from different breeds or lines of cattle. Thus, typically, 50% of the autosomal genome (e.g., the somatic genome) of a hybrid is from a first breed/line, and 50% is from a second breed/line. Of particular interest, as described herein, are hybrids in which 50% of its somatic chromosomes are from a first breed and 50% are from a second breed.

In Vitro Fertilization (IVF): As used herein, the term "in vitro fertilization" refers to a method of fertilizing an egg outside of living cattle. IVF is a process by which an egg is fertilized by sperm outside the body (i.e., in vitro, which literally translates to "in glass" but is understood in the art to refer to processes performed, for example, in a laboratory or other artificial setting). In some embodiments, an IVF process may involve monitoring and/or stimulating a female's ovulatory process, removing oocyte or oocytes (egg or eggs) from a female's ovaries, and/or contacting sperm and oocytes with one another in a laboratory (e.g., in a fluid medium) to achieve fertilization. In some embodiments, IVF involves culturing a fertilized egg (zygote) in a growth medium and/or either implanting it in a female's uterus or storing it for future analysis and/or implantation. In some embodiments, IVF may involve sorting fertilized eggs for particular desired attributes (e.g., gender).

Line: As used herein, the term "line" refers to a strain of cattle descended from common ancestral parents developed and maintained by selective breeding.

Mating: The term "mating," as used herein, refers to a process that results in formation of an embryo, typically from two opposite-gender gametes. In some embodiments, mating involves natural service. In some embodiments, mating involves artificial insemination. In some embodiments, mating involves IVF. In many embodiments described herein, mating is utilized to generate hybrid progeny. In many embodiments, mating is utilized to generate crossbreed progeny.

Natural Service: As used herein, the term "natural service" refers to traditional cattle breeding of pairing males and females without artificial insemination or IVF-based techniques.

Phenotype: As used herein, the term "phenotype" refers to a trait, or to a class or set of traits displayed by a cell or organism. In some embodiments, a particular phenotype may correlate with a particular allele or genotype. In some embodiments, a phenotype may be discrete; in some embodiments, a phenotype may be continuous.

Single Nucleotide Polymorphism (SNP): As used herein, the term "single nucleotide polymorphism" or "SNP" refers to a particular base position in the genome where alternative bases are known to distinguish one allele from another. In some embodiments, one or a few SNPs and/or copy number polymorphisms (CNPs) is/are sufficient to distinguish complex genetic variants from one another so that, for analytical purposes, one or a set of SNPs and/or CNPs may be considered to be characteristic of a particular variant, trait, animal, line, breed, cross-breed, or set thereof. In some embodiments, one or a set of SNPs and/or CNPs may be considered to define a particular variant, trait, animal, line, breed, cross-breed, or set thereof.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Trait: As used herein, the term "trait" refers to a detectable attribute of an individual. Typically, expression of a particular trait may be fully or partially influenced by an individual's genetic constitution. In some embodiments, a trait is characteristic of a particular individual, line, breed or crossbreed, for example in that it can be relied upon (individually or as part of a set) to distinguish that individual, line, breed, or crossbreed from others.

Detailed Description of Certain Embodiments

Dairy Cattle

Remains of domesticated cattle dating to 6,500 B. C. have been found in Turkey and other sites in the Near East approach this age also. Some authorities date the domestication of cattle as early as 10,000 years ago, and others almost half that amount of time. Early cattle served a triple-purpose. They provided meat, milk, and labor to their owners. Eventually their labor/draft purposes were largely replaced by horses and machinery so they were selected more for single or in some cases dual purposes (milk and meat).

The Ayrshire breed originated in the County of Ayr in Scotland, prior to 1800. Ayrshires are medium-sized cattle and should weigh over 1200 pounds at maturity. They are strong, rugged cattle that adapt to all management systems including group handling on dairy farms with free stalls and milking parlors. Ayrshires excel in udder conformation and are not subject to excessive foot and leg problems. Few other breeds can match the ability of the Ayrshire to rustle and forage for themselves under adverse feeding or climatic conditions. Ayrshire cattle will do better under pasture conditions than will the other major dairy breeds and, when pastures are poor, they need less grain to keep them in air condition (C. H. Eckles, *Dairy Cattle and Milk Production*, 1923). The ruggedness of the terrain and the unfavorable climatic conditions of their native land led to the selection for those points of hardiness that adapt them to less than ideal conditions. These traits make Ayrshires outstanding commercial dairy cattle.

The Ayrshire is a moderate butterfat breed. The actual average of all Ayrshires on the official Dairy Herd Improvement Registry (DHIR) test is over 12,000 pounds of milk per year with a 3.9% test. Ayrshires respond to good management and feeding practices and individual Ayrshire herds average as high as 17,000 pounds of milk per year and 700 pounds of butterfat. Top producing Ayrshires regularly exceed 20,000 pounds of milk per year in their lactations.

Other traits that make Ayrshires attractive to the commercial dairyman include the vigor of Ayrshire calves. They are strong and easy to raise. Ayrshires do not possess the yellow tallow characteristic that would reduce carcass value, so Ayrshire bull calves can be profitably raised as steers.

The Guernsey cow is known for producing high-butterfat, high-protein milk with a high concentration of beta-carotene. Being of intermediate size, Guernseys produce their high quality milk while consuming 20 to 30 percent less feed per pound of milk produced than larger dairy breeds. They are also known for having a lower projected calving interval and have a younger average age of first calf heifers than the larger breeds. Other attractive characteristics of Guernseys are their lack of any known undesirable genetic recessives and their adaptability to warmer climates.

The Guernsey is also an excellent grazer. The cow is made for pasture-based milk production. Because of its grazing abilities, gentle disposition, calving ease, and ability to efficiently produce milk with less feed than other breeds, it is the ideal candidate for intensive grazing. Dairy producers can realize profit potential while reducing management costs.

Data from herds enrolled in the American Guernsey Association's DHIR program during 1992 shows the breed average to be 14,667 pounds of milk, 659 pounds of butterfat and 510 pounds of protein per year on a mature-equivalent basis.

Genetically, the Guernsey of today is much different than that of 960 A. D. Due to the advent and commercialization of artificial insemination, a process by which semen is introduced into a dam by other than natural means, a particular bull can sire thousands of offspring. This genetic improvement has been generated by a progressive, aggressive young sire program. Young bulls' semen is distributed throughout the Guernsey population until the bulls have a large enough daughter population that their offsprings' qualities are predictable. As proven bulls, these sires may have as many as 1,500 daughters in up to 400 herds.

However, every six months the list of available sires is updated. At that time, new bulls with superior genetics are added and older sires lose their "active" status. This insures that the breed-wide effort to improve the Guernsey's sound genetic base continues.

The Holstein cow originated in Europe. The major historical development of this breed occurred in what is now the Netherlands and more specifically in the two northern provinces of North Holland and Friesland which lay on either side of the Zuider Zee. The original stocks were the black animals and white animals of the Batavians and Friesians, migrant European tribes who settled in the Rhine Delta region about 2,000 years ago. For many years, Holsteins were bred and strictly culled to obtain animals which would make best use of grass, the area's most abundant resource. The intermingling of these animals evolved into an efficient, high-producing black-and-white dairy cow.

A healthy Holstein calf weighs 90 pounds or more at birth. A mature Holstein cow weighs about 1500 pounds and stand 58 inches tall at the shoulder. Holstein heifers can be bred at 15 months of age, when they weigh about 800 pounds. It is desirable to have Holstein females calve for the first time between 24 and 27 months of age. Holstein gestation is approximately nine months. While some cows may live considerably longer, the normal productive life of a Holstein is six years. Average production for all Holsteins enrolled in official U.S. production-testing programs in 1987 was 17,408 pounds of milk, 632 pounds of butterfat and 550 pounds of protein per year.

The Jersey breed originated on the Island of Jersey, a small British island in the English Channel off the coast of France. The Jersey is one of the oldest dairy breeds, having been reported by authorities as being purebred for nearly six centuries. The breed was known in England as early as 1771 and was regarded very favorably because of its milk and butterfat production.

Adaptable to a wide range of climatic and geographical conditions, outstanding Jersey herds are found from Denmark to Australia and New Zealand, from Canada to South America, and from South Africa to Japan. They are excellent grazers and perform well in intensive grazing programs. They are more tolerant of heat than the larger breeds. With an average weight of 900 pounds, the Jersey produces more pounds of milk per pound of body weight than any other breed. Most Jerseys produce far in excess of 13 times their bodyweight in milk each lactation.

The American-type Jerseys were noted much more for production than for beauty. Cattle referred to by this description are usually larger, a bit coarser, and have been bred for years for those qualities that suit them for milk and butterfat production. Additional emphasis on milk production and less stress on butterfat production had, no doubt, resulted in general acceptance of Jersey cows with more size and scale. Recent importations of Jerseys have consisted of larger cattle than many previously brought to the United States. Their offspring have not only been acceptable in type but have also been used advantageously in improving production.

One of the oldest recognized breeds in the world, Shorthorn cattle originated in Northeastern England in the Valley of the Tees River. The Milking Shorthorn breed is the most versatile of all breeds and this is one of its greatest attributes. These docile cows efficiently produce large volumes of nutritious milk each lactation and are large enough to have a high salvage value when their long productive lives finally come to an end. In addition, their healthy calves born each year on regular calving intervals are spunky at birth, grow rapidly, and those not kept for breeding stock and herd replacement make efficient gains and hang very desirable grading carcasses. Other attributes of the breed include ease of calving, ease of management and economy of production, especially on home produced roughages and grass.

Belarus Red, also known as Byelorussian Red, Krasnaya belorusskaya, and Krasnobelorusskaya, is a Russian dairy cattle breed. The breed has been improved by crossing with Angeln Red, German Red, Polish Red, Danish Red, Estonian Red, and Latvian Brown. They are common in Belarus, mostly around Grodno and Minsk. They are noted for their longevity and undemanding feeding requirements.

The appearance of the Belarus Red cows is characterized by the following features. The head is medium long, not wide, with a long face. The poll is pronounced. The horns are of medium size. The neck is thin and of moderate length. The withers are not sharp, occasionally divided. The chest is of medium depth, wide enough. The back is level, slightly narrow. The loin is long and level, of medium width. The mid-part of the body is well developed. The abdomen is capacious, not drooping. The rump is level, slightly raised. The hindquarters are of medium length and width, with protruding hips. The legs are comparatively thin, bony, not long, correctly set. Sometimes legs are splayed or bowed. The udder is medium in volume, glandular, cup-shaped or roundish. The teats are cylindrical, of medium size. The skin is thin, elastic, mobile. The skeleton is light and strong. The musculature is moderately developed. The conformation is harmonious and compact; the constitution delicate.

Many consider that the potential of the modern Belarus Red cattle has not been completely realized. The average milk yield of Belarus Red stock evaluated at the breeding farms in 1981 was 2557 kg with 3.69% fat; at the best farms it was 3053 kg with 3.62% fat. In the herd of the Vasilishkovski breeding center in the Grodno region the average milk yield in 1982 was 2507 kg with 3.73% fat. In recent years several groups of cows of this herd and of the Shchuchin experimental station averaged 4514 kg of milk with 4.08% fat. In her 4th lactation cow Vyetv 2016 produced 5986 kg of milk with 3.91% fat and 3.70% protein; Malta produced in her 3rd lactation, 6056 kg of milk with 4.55% fat; Volna produced, in her 4th lactation, 5906 kg with 4.85% fat.

Beef and fattening qualities of Belarus Red cattle are satisfactory: under favorable conditions of feeding and management the young stock display a high growth rate and early maturity. The breed comprises 6 basic lines and 2.'D families. To preserve these cattle conservation herds have been set up and a bank of frozen semen of the best sires of all basic lines has been established. The breeding program for the improvement of Belarus Red cattle aims at the following parameters for the purebreds: the live weight of mature cows should be 500-540 kg, the milk production per lactation should be 4.5-5.0 thousand kg with fat content of 4.0-4.2% and protein content not less than 3.6%.

The Belted Galloway is a heritage beef breed of cattle originating from Galloway in the west side of southern Scotland, adapted to living on the poor upland pastures and windswept moorlands of the region. The exact origin of the breed is unclear although it is often surmised that the white belt that distinguishes these cattle from the native black Galloway cattle may be as a result of cross breeding with Dutch Lakenvelder belted cattle. It is the belt that gives them their name. Belted Galloways (or Belties) are primarily raised for their quality marbled beef, although they are sometimes milked and purchased to adorn pastures due to their striking appearance.

Galloway cattle are naturally polled. Particularly visible characteristics of the Belted Galloway are its long hair coat and the broad white belt that completely encircles the body. Its coarse outer coat helps shed the rain, and its soft undercoat provides insulation and waterproofing, enabling the breed to happily overwinter outside. Black Belties are most prominent, but Dun and Red Belties are also recognized by breed societies, the latter being comparatively rare and sought after. A female Belted Galloway cannot be registered in the Herd Book if it has white above the dewclaw other than the belt, but can be registered in the Appendix. A bull can only be registered in the Herd book if it has no other white than the belt.

Bulls weigh from 1,700 pounds (770 kg) to 2,300 pounds (1045 kg) with the average being 1,800 pounds (820 kg). Cows weigh from 1,000 pounds (450 kg) to 1,500 pounds (675 kg) with the average being 1,250 pounds (565 kg). Calves generally weight from 40 pounds to 60 pounds.

Belties are generally of a quiet temperament, but still maintain a strong maternal instinct and will protect a calf against perceived threats. Belties are well-suited for rough grazing land and will utilize coarse grasses other breeds would shun. They are able to maintain good condition on less than ideal pasture, and produce a high quality beef product on grass alone. The USDA Cycle IV Germ Plasm Evaluation Program at the Meat Animal Research Center (MARC) showed that Galloway crosses placed at the top of the chart for flavor, juiciness, and tenderness when compared to eleven other breeds.

Brown Swiss is a breed of dairy cattle that produces the second largest quantity of milk per annum, over 9,000 kg (20,000 lb.). The milk contains on average 4% butterfat and 3.5% protein, making their milk excellent for production of cheese. The Brown Swiss is known for a long gestation period, immense size, large furry ears, and an extremely docile temperament. Regardless, the Brown Swiss is quite a resilient breed of cattle; they are hardy and capable of subsisting with little care or feed.

The Brown Swiss originated on the slopes of the Alps in Switzerland; because they were bred in this harsh climate, they are resistant to the heat, cold and many other common cattle problems.

Norwegian Red (Norwegian: Norsk rødt fe) is a breed of dairy cattle developed in Norway. Often shortened to simply NRF, it has a red and white or black coat. Norwegian Reds are noted for their hardiness and the richness of their milk.

Norwegian Red (NRF) is a dairy breed that has been selected for a broad breeding objective, with increasing emphasis on functional traits like health and fertility. NRF—Norwegian Red was developed in the 1960s through crosses of dairy breeds with several Scandinavian breeds, including the Norwegian Red-and-White, Red Trondheim, and the Red Polled Ostland. By the mid-1970s it became the dominant breed in its native country, comprising 98% of the cattle population. Semen is frequently also exported to North America for crossbreeding with Holstein cattle in the U.S. dairy industry. Geno Breeding and A. I. Association, a cooperative organization owned by Norwegian dairy farmers, is the breeding organization for the Norwegian Red.

Production in the best herds exceeds 10,000 kilograms (22,000 lb.), with the top cows milking more than 16,000 kilograms (35,000 lb.). Growth traits are also included in the index, and young sires for progeny testing have a growth rate of approximately 1.4 kg/day. Fully-grown cows have a live weight of up to 600 kilograms (1,300 lb.).

Health traits have been included in the net merit index since 1978. Currently mastitis and other diseases (in particular ketosis) are included in the breeding program. Although these are low heritability traits, progeny testing based on a high number of daughters provides a selection index with high accuracy. Progeny testing for mastitis is currently based on approximately 300 daughters.

Norwegian Reds may be either polled or horned. Currently 50% of the calves in Norway are born polled (genetically without horns). Systematic selection of polled sons after polled elite sires during recent years have increased the frequency of polled animals. It is expected that Norwegian Red (NRF) breed will become a polled breed within the next 20-25 years.

Conventional Dairy Cattle Husbandry

Animal husbandry is the management and care of farm animals by humans for profit, in which genetic qualities and behavior, considered to be advantageous to humans, are further developed. The term can refer to the practice of selectively breeding and raising livestock to promote desirable traits in animals for utility, sport, pleasure, or research.

Animal husbandry combines the art and science of raising animals by blending time-honored practices and modern scientific knowledge into a system that provides for animal well-being and provides for safe and efficient management and handling of animals. Animal husbandry practices change as scientists, agricultural experts, and others involved with animals learn new techniques or phase out those that are no longer necessary or appropriate. Animal husbandry practices range from dehorning cattle to prevent injury to herd-mates and farm hands to methods for housing livestock, providing adequate nutrition, and devising breeding strategies.

Techniques such as artificial insemination and embryo transfer have been developed and can be used to facilitate breeding. For example, because such technologies permit a dam to carry an embryo other than her own, they can be used to ensure that large numbers of embryos from a particular high quality dam (or dam line) can be implanted into a lower-quality surrogate, thereby expanding the number of progeny that can be generated from the high-quality dam. This practice can vastly increase the number of offspring which may be produced by a small selection of the best quality parent animals. However, as discussed herein, such technologies have not typically been employed with dairy cattle. Among other things, they are often deemed to be too expensive to warrant use with dairy cattle. Also, to the extent that they tend to amplify particular genetic traits within a herd, they decrease genetic diversity within the herd, increasing the severity of certain disease outbreaks among other risks. Among other things, the present invention encompasses the insight that such techniques, particularly when combined with crossbreeding strategies, can provide significant advantages in the husbandry of dairy cattle as compared with conventional approaches.

In general, the present disclosure encompasses the recognition that present day dairy farming has become a high risk business with very low returns on invested money. There is very little room for mistakes or extra expenses. Among other things, the cost of replacement females for a cow-calf operation is significant. Selecting replacement females is challenging, especially when you consider that decisions made now will impact your operation for many years. Therefore, dairy farmers have to find ways to be as efficient with expenses and resources as possible. Ideally, dairy farmers need to maximize milk production and find ways to guarantee stable, high milk production from generation to generation.

Conventional Selection of Breeding Stock

In conventional animal husbandry approaches to breeding dairy cattle, dairy producers have a multitude of informational inputs available to make sire selection decisions. For example, predicted transmitting abilities (PTAs) can be computed for various traits, for example in the broad categories of production (milk and milk components), health/fitness, and type. Also, every 3 months, the Animal Improvement Programs Laboratory (AIPL) of the United States Department of Agriculture releases the newest USDA-DHIA (Dairy Herd Improvement Association) genetic evaluations for dairy bulls and cows. Dairy cattle are evaluated for the traits of milk, fat, and protein yield, length of productive life, and somatic cell score (an indicator of mastitis). Evaluation procedures combine information from all known female relatives of an evaluated animal, and from the animal itself in the case of cows. Additionally, numerous type or conformation traits are evaluated routinely. The AIPL calculates genetic evaluations for type for various breeds, and many breed associations provide their own indexes or other strategies for evaluating certain breed-relevant traits.

Traits are typically combined into an index based on their relative economic weights. For example, the Net Merit index (NM$) computed by USDA AWL estimates lifetime profit based on incomes and expenses relevant for today's dairy producers and is expressed as a dollar value. Traits included in NM$ are: protein (lb.), fat (lb.), productive life, somatic cell score, udder composite, feet/legs composite, body size composite and daughter pregnancy rate. Calving ability also is included in NM$ calculations for Holsteins and Brown Swiss. The traits incorporated into calving ability for Holsteins are daughter stillbirth, service sire stillbirth, daughter calving ease, and service sire calving ease. Only the two calving ease traits are available for inclusion in calving ability values of Brown Swiss.

Selection indexes developed by the various dairy breed associations typically reflect genetic goals determined by their respective boards of directors. The U.S. Ayrshire Breeders' Association uses a Production Type Index (PTI) as a ranking tool for Ayrshire bulls. This index accounts for protein, fat, type, daughter pregnancy rate, udder depth and somatic cell score. The Progressive Performance Ranking (PPR) is the selection index used by the Brown Swiss Association. Traits included in the PPR are protein, fat, somatic cell score, productive life, foot and leg composite, udder composite and daughter pregnancy rate. The selection index developed by the American Guernsey Association is the Production Type Index (PTI). Traits combined in the PTI are: protein, fat, type, udder composite, foot and leg composite, productive life, daughter pregnancy rate, somatic cell score, and strength. Holstein Association USA calculates the Total Performance Index (TPI). It includes the traits of protein, fat, type, udder composite, feet and leg composite, daughter pregnancy rate, productive life, somatic cell score, daughter calving ease, daughter stillbirth and dairy form. The Jersey Performance Index, which is used by the American Jersey Cattle Association, is comprised of the following traits: protein, fat, functional trait index, productive life, somatic cell score, and daughter pregnancy rate. Functional trait index is based on the bull/cow PTAs for all type traits.

Using a selection index can be an effective way to consider several traits when choosing breeding stock. Conventional animal husbandry strategies often rely on selection indexes, particularly for choosing service sires.

Conventional Sire Selection Strategies

Breeding stock sires and sire lines are typically chosen based upon their size and fertility. Prior successes in mating as well as siring females are both traits that are often utilized in selecting sires and/or sire lines.

Also, knowing where service sires rank relative to other active bulls is typically considered to be helpful in determining if the sires meet a particular herd's genetic goals. Selection indexes can be particularly useful in monitoring such ranking. To maximize genetic improvement using a selection index, it is usually recommended that the service sires for a given herd average at or above the 80th percentile.

Under conventional sire selection principles, sires of males (SM) represent the most elite males that are selected to be sires of the next generation of young bulls. This group is chosen based on estimated breeding value (EBV) or genomic estimated breeding value (GEBV), and is typically composed of <5% of the males whose semen is marketed to dairy farmers. These bulls are often referred to as "sires of sons."

In accordance with these same conventional sire selection principles, sires of females (SF) represent a larger group of males that have been selected based on EBV or GEBV and whose semen is used to breed the general population and produce replacement females for commercial farms. These bulls are typically referred to as "active AI sires."

Conventional Dam Selection Strategies

In conventional animal husbandry approaches to breeding dairy cattle, breeding stock dams and dam lines are typically chosen based upon their milk production capabilities and their fertility.

Under conventional dam selection principles, dams of males (DM) represent a group of elite females that are selected based on EBV or GEBV and that usually rank among the top 1% of the population. These cows are typically mated to elite bulls from the SM group for the purpose of producing bull calves, and they are more commonly referred to as "bull mothers."

In accordance with these same conventional dam selection principles, dams of females (DF) represent the large population of females that are primarily used to produce milk rather than breeding stock. These cows, which are often referred to as "commercial cows," are routinely mated to bulls from the SF group to initiate lactation, resulting in the next generation of replacement heifers.

Known Benefits of Cross Breeding

Practitioners of animal husbandry are well aware that many advantages are commonly observed with crossbreeding, are well documented, and can have a big impact on net return. Heterosis (hybrid vigor) and breed complementarity are the primary benefits realized from a properly planned crossbreeding program. Specifically, heterosis refers to the increase in performance or function observed in crossbreed hybrid progeny that is above what is expected based on the parents of the offspring. Breed complementarity allows a breeder to capitalize on the strengths of different breeds because no single breed excels at all of the traits that affect profitability.

Heterosis can be observed with respect to any health or production traits if there is sufficient genetic difference between the two breeds being crossed. If Breed 1 is crossed with Breed 2 the added benefit beyond the average of both breeds' traits witnessed in the offspring is the heterosis effect. The heterosis effect can be variable between breeds and also across traits that are affected.

Maternal heterosis is the advantage realized by using a crossbred cow versus a straight-bred cow. Research has shown that crossbred hybrid cows can have many advantages, which can include, for example, higher calving rate (increases of about 6% are commonly reported), higher calf survival rate (increases of about 4% are commonly reported), higher calf weaning weight (increases of about 5% are commonly reported), higher post-weaning calf gain (increases of about 6% are commonly reported), higher milk production (increases of about 6% are commonly reported), higher efficiency (increases of about 8% are commonly reported), increased longevity (increases of about 38% are commonly reported), and increased lifetime productivity (increases of about 23% are commonly reported). Those skilled in the art are aware that presence or level of any particular benefit can vary greatly in different crosses, and are generally believed to be significantly influenced by breed.

The goal of most commercial cow-calf producers is to increase profitability. While it is appreciated that using crossbreeding can have a significant positive impact on various aspects of production in a dairy farm, including healthier and more fertile offspring as well as the ability to introduce genetic diversity into the herd, it is also understood that conventional crossbreeding strategies can produce cattle of inferior, instead of superior, quality or with unexpected negative traits. One of the challenges encountered with traditional crossbreed farming is that crossbreeds include the potential for unpredictable behavioral traits, such as temperamental dispositions; such undesirable traits can be amplified if crossbred hybrid animals (i.e., "F1" progeny) are subsequently in-bred or back-crossed in an effort to continue a line.

The present disclosure appreciates that crossbred herds are difficult to maintain. That is, there is a risk of losing high performing traits of F1 cattle. For example, if farmers try to maintain an F1 herd using conventional approaches (e.g., as depicted in FIG. 1), they will typically mate females of the herd to the F0 sire (see FIG. 1, left panel). However, loss of hybrid vigor with respect to particular desirable typically results from such backcrossing. Such backcrossing can also result in increased heterogeneity in the next generation of animals due to independent assortment of alleles in the parents. An alternative strategy to cross breeding has been to introduce a third breed as the mating sire for the F1 hybrid animals (see FIG. 1, right panel). While this strategy has higher relative heterosis compared to the backcrossing strategy it still suffers from the problem of independent assortment that results in unpredictable and highly varied phenotypes. The present disclosure, among other things, encompasses the insight that there is currently a problem with crossbreeding systems in that the initial, high performing and uniform F1 hybrid animals cannot be used to make similarly high performing and uniform replacements with natural service or artificial insemination due to segregation of alleles in the production of gametes from the F1 parent.

Inventive Strategies for Generating and/or Maintaining F1 Crossbreed Dairy Cattle The present disclosure encompasses the insight that, while dairy producers can already benefit from F1 genetics, dairy herds would benefit from an ability to support the production of their replacement from pregnancies occurring in the normal course of their dairy operation. Pregnancies produced on hybrid cattle with current methods (artificial insemination or natural service) result in unpredictable offspring due to recombination during the natural processes that create haploids (eggs) in the hybrid animals. The present disclosure provides new approaches that permit production and/or maintenance of valuable F1 crossbreed dairy cattle herds.

Among other things, the present invention encompasses the recognition that an improved system for providing and/or maintaining cross-bred dairy cattle herds involves identifying, characterizing, and/or selecting one or both F0 individuals or lines based on performance of their hybrid progeny.

As discussed herein, the superiority of hybrid animals (aka "F1 cross-breeds") has been documented in the academic literature for decades. Despite evidence of superiority, cross breeding systems and use of F1s specifically constitute a small percentage of total dairy operations. The present disclosure encompasses the insight that, where cross breeding systems fail is in the production of the next generation of replacements. The F1 animal itself is a composite that has 50% of its genome from Breed A and 50% from Breed B. Its phenotype and performance is therefore consistent. With natural or AI delivery the next animal produced (the replacement) from this female presents challenges. Due to simple Mendelian principles of independent assortment the Breed A and Breed B contributions will recombine in the production of haploids for the next generation, and while on aggregate these haploids will be 50% A and 50% B the actual contribution will be a normal distribution centered at 50% A:B and approach 100% at the tails. Since every replacement pregnancy will be a single draw from this distribution you will not likely get the middle AND every draw will get different genes represented from A or from B. Thus the haploid oocytes produced even if mated to a SINGLE SIRE will differ markedly from each other in phenotype, performance, and even simple cow design. For this reason the usual end of a crossbreeding operation is a return to one of the original F0 parent breeds through a system of recurrent backcrossing, or through simple acquisition of purebred animals from outside the operation (see FIG. 1 and FIGS. 2A-2D). A business system that could sustainably deliver hybrid F1 genetics, while generating the pregnancies required for sustained milk production has potential for wide adoption and positive impact throughout the dairy industry.

Figure 3:
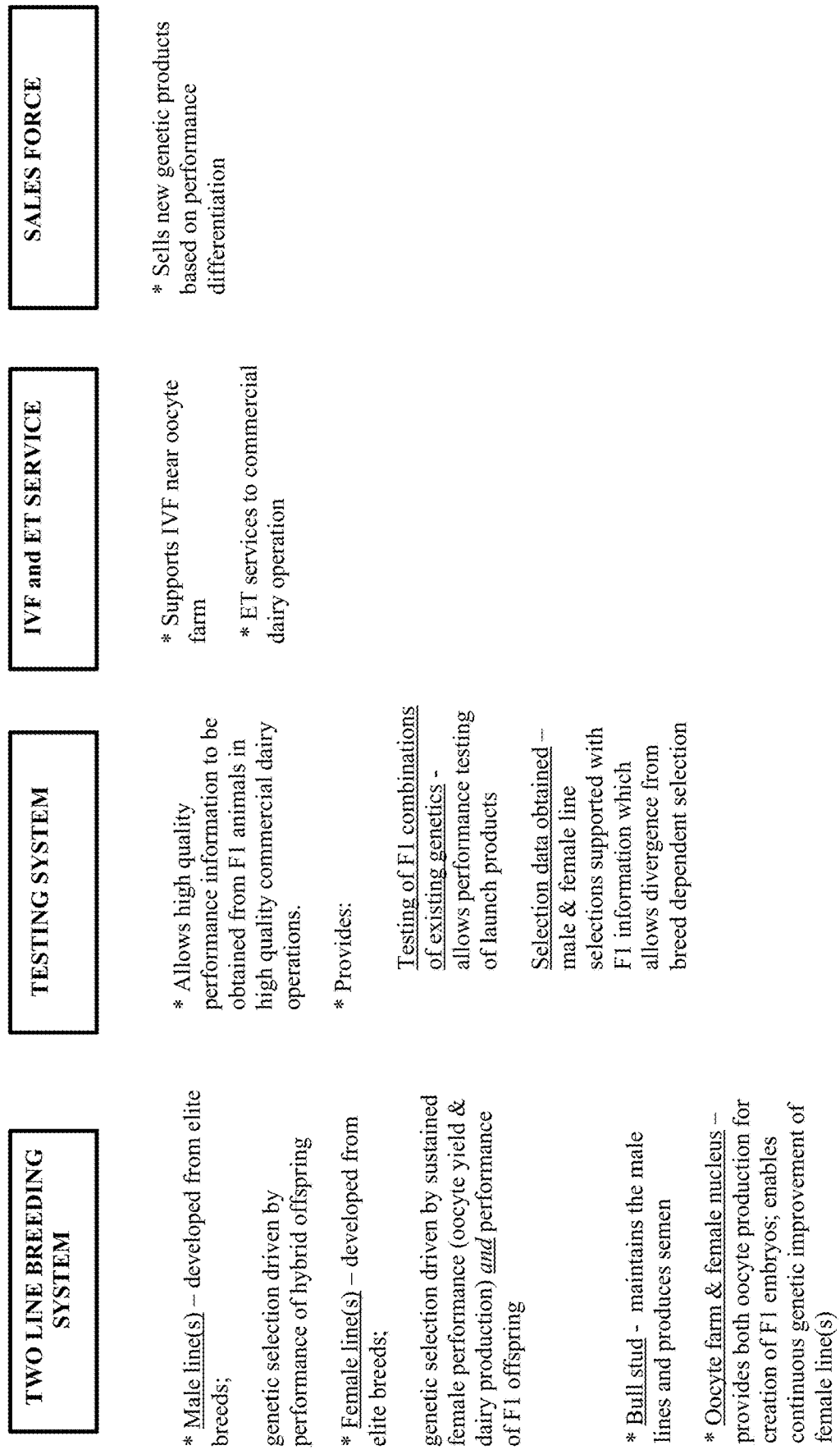
FIG. 3 outlines an inventive system for providing valuable valued products and services to dairy customers based upon embodiments of the present disclosure. Components of the depicted system include: 1) a two line breeding system; 2) a testing system; 3) an IVF and ET transfer service; and 4) a sales force.

In accordance with the present disclosure, a system to deliver this value can be assembled from the following components. (1) A two line breeding system incorporating one or more: (a) male line(s)—which are developed from current elite dairy breeds to provide semen and are developed in a manner similar to the development of current AI sires with the exception that genetic selection is driven by performance (predicted and measured) of the hybrid offspring; (b) female line(s)—which are also developed from current elite dairy breeds to provide oocytes to be used in WF. These lines are developed with indexed based genetic selection based on sustained female performance (in terms of oocytes yield and diary performance) and performance of the F1 offspring; (c) a bull stud to maintain the male lines and produce semen; (d) an oocyte farm and female nucleus that provides both oocyte production for creation of F1 embryos and allows continuous genetic improvement of the female line(s). (2) A testing system that allows high quality performance information to be obtained from F1 animals in high quality commercial dairy operations to provide: (a) testing of F1 combinations of existing genetics to allow launch products to be performance tested; (b) selection data to be obtained so the male and female line selections can be supported with F1 information and can diverge from breed dependent selection. (3) An IVF and embryo transfer (ET) service business that can support IVF in proximity to the oocytes farm and ET services to dispersed commercial dairy operations. (4) A customer facing sales force that can sell new genetic products based on performance differentiation. See FIG. 3.

In some embodiments, generating and/or maintaining high performing hybrid F1 dairy cattle involves use of modern reproductive technologies such as IVF, ET, artificial insemination, cryopreservation, and nuclear transfer among others. Such modern techniques have been used in industries such as race horse breeding, where pure-bred animals are quite valuable, but not in the dairy industry [for the production of crossbreeds], where individual commercial production animals (i.e., females) are typically considered to be of insufficient individual value to warrant use of such technologies.

In some embodiments, the present invention encompasses the use of modern technologies such as IVF, ET, artificial insemination, cryopreservation, and nuclear transfer in the screening, generation, and maintenance of hybrid dairy cattle.

Furthermore, in some embodiments, the present invention provides technologies through which gamete samples from an F0 sire are mated to a first plurality of female gametes from a first F0 dam, and also to a second plurality of female gametes from a second F0 dam, different from the first F0 dam, but optionally of the same line as the first F0 dam). In many embodiments, each of the first and second F0 dams is of a different breed from the F0 sire. Traits of hybrid progeny from each of these first and second (and subsequent) cross-breed crosses are assessed, and the F0 sire (and optionally one or more of the F0 dams or dam lines) is selected for use in subsequent cross-breed matings based on desirable performance of F1 progeny from the first and/or second cross-breed crosses.

In some embodiments, the quality of hybrid progeny traits is assessed relative to that of a reference animal. In some embodiments, the quality of hybrid progeny traits is assessed relative to that of hybrid progeny of comparable cross-breed cross (optionally historical or simultaneous). In some embodiments, the quality of hybrid progeny traits is assessed with reference to a crossbreed index or other industry standard.

In some embodiments, the present invention provides for continual [generation on generation] improvement of hybrid herds due to ongoing monitoring of performance of hybrid crossbreed progeny traits, and comparison with those of hybrid crossbreed progeny of other dairy cattle crosses, so that periodic or continual improvements can be made in selection of F0 breeding stock.

In some embodiments, F1 embryos may be shipped from a first farm that is a stud farm to a second farm that is a gestational dam farm having a herd of gestational cows into which semen or embryos can be delivered. In some embodiments, F1 embryos can be shipped to a plurality of different gestational farms, so that a plurality of F1 progeny herds is produced at the plurality of farms. In some embodiments, information regarding F1 traits is provided by the gestational farm(s) (or by purchasers of one or more of the F1 progeny cattle) to the stud farm so that quality of the sire as breeding stock for hybrid dairy cattle can be assessed. Analogously, in some embodiments, information regarding hybrid traits is provided to one or more of the gestational farm(s) and/or to the source farm of the F0 gamete used to generate the F1 embryos so that quality of the dam or dam line as dairy cattle breeding stock can be assessed.

In some embodiments, assessment of F1 traits in progeny of one or more matings of gametes from particular F0 individuals or lines may be assessed at multiple points in time so that quality of F0 individuals as dairy cattle breeding stock can be periodically or continually reassessed. In some embodiments, one or more particular F0 individuals may be de-selected over time as dairy cattle breeding stock.

Inventive Selection of Breeding Stock/Hybrid Breeding Indeces

In some embodiments, in accordance with the present invention, F0 cattle may be selected based upon the performance of hybrid cattle that result from cross-breed matings of their gametes. For example, the milk production performance of hybrid cattle can be evaluated, and F0 cattle may be selected for use as breeding stock for a particular cross (e.g., for a cross-breed cross) based on the performance of their F1 progeny from prior cross-breed crosses.

Alternatively or additionally, hybrid traits that may be evaluated may include, for example, age at first calving, body depth, cell counts, cow conception rate, dairy form, daughter calving ease, daughter pregnancy rate (the rate at which F1 animals become pregnant with daughters), daughter still birth, fat pounds, milk fat percent feet and legs score, fertility, final score, foot angle, fore udder attachment, front teat placement, heifer conception rate, ketosis, lameness rate and/or degree, locomotion, milk productive life, milking speed, milk protein percent, protein pounds, rear legs rear view, rear legs side view, rear teat placement, rear udder height, reproductive life, resistance to cold, resistance to disease (e.g., mastitis, metritis, etc.), rump angle, rump width, somatic cell score, sire calving ease, sire still birth, size, stature, strength, teat length, udder cleft, udder conformation, udder depth, and combinations thereof.

Hybrid traits may be evaluated on the basis of phenotype, genotype, or both, using any available techniques.

One or more hybrid traits may be utilized in one or more hybrid indexes; such hybrid indexes may facilitate organization, evaluation, and/or ranking of hybrid cattle, which in turn may facilitate selection of F0 individuals or lines based on performance of their hybrid progeny. In some embodiments, relative weights are assigned to individual traits (e.g., within an index).

In some embodiments, milk production is deemed the most influential (e.g., heavily weighted) hybrid trait considered for selection of F0 individuals or lines. In some embodiments, one or more of infertility, high somatic cell counts, and lameness is assigned a negative weight (e.g., is selected against) in an inventive method or index.

Among other things, technologies provided by inventive strategies described herein are expected to maximize milk production and/or to minimize turn-over or replacement rate in hybrid herds.

In some embodiments, reduced susceptibility to disease may be a key performance trait for evaluating hybrid cattle. Mastitis is an infection of the udders that negatively impacts milk production. Selecting against mastitis can improve the milk producing capabilities of the hybrid cattle. High somatic cell counts are also an indicator of an infection like mastitis. Selecting against high somatic cell counts (SCC) can lower the incidences of disease.

Fertility is one of the major factors affecting the efficiency of any dairy herd. It can account for one of the major costs of production and also represents an area where significant improvements can be made. Poor dairy herd fertility is recognized as having many consequences, both direct and indirect. Most importantly: loss of milk production through too many dry days or peak yield traded for later lactation yield; disruption to the calving season and milk production pattern; loss of mature animal milk yields through early culling; extra veterinary costs; reduced calf sales; additional AI costs; enforced culling resulting in more replacements being reared or bought; loss of valuable genetics; and linkage with other problems such as nutritional imbalances and production shortfalls. The first step in reducing unnecessary fertility losses is detailed assessment of individual herd fertility performance as well as selecting for F0 that will improve or maintain desired fertility.

In some embodiments, desirable hybrid traits may include potential suitability as a beef cow. Dairy females that are no longer able to produce milk are traditionally culled in favor of replacement females. Traditionally, dairy cows do not often provide meat of a quality in line with beef cattle, sometimes leading to reduced value for the cattle. Having traits desirable to the beef markets would provide another source of profitability to dairy farmers. In some embodiments, dairy cattle cross-bred with beef cattle have traits desirable to the beef industry without sacrificing traits valuable to milk production.

In some embodiments, gametes from breeding stock males and/or females selected based on performance of hybrid progeny resulting from prior crossbreed crosses are utilized to produce new hybrid embryos and/or hybrid progeny. In some embodiments, such gametes are collected for storage (e.g., freezing/cryopreservation). In some embodiments, such gametes are sold, for example to one or more farms or farming facilities.

In some embodiments, further breeding progress is obtained where both sire and dam lines contribute to the F1 performance by selecting traits separated between the two lines. For example, in a hybrid animal resulting from a combination of Holstein and Jersey breeds, where the Holstein is the sire line and the Jersey is the dam line, the Holstein parent can be selected with a focus on fluid milk production, while ignoring milk components and the Jersey parent can be selected with a focus on milk solids (e.g. fat and protein), for example optionally ignoring fluid milk production. In this way, further genetic progress can be made than by trying to improve both traits in each of the parent lines.

Thus, the present disclosure provides selection strategies for breeding cattle that differ from those used in conventional dairy cattle husbandry. Those skilled in the art, reading the present disclosure, will appreciate that it therefore also provides novel breeding indices for cattle breeds that are specifically tailored for generating quality hybrid progeny (such indices may be referred to herein as "hybrid breeding indices"). For example, with respect to the particular case described in the prior paragraph, the present disclosure provides a hybrid breeding index for a Holstein parent to be used in a Holstein/Jersey cross that focuses on milk production and not milk components; and also provides a hybrid breeding index for a Jersey parent to be used in such a cross that focuses on milk solids and not milk production. Those skilled in the art will further appreciate that, in accordance with the present disclosure, different hybrid breeding indices may be utilized for a given strain or line depending on the partner strain or line to be utilized in the cross. The present invention therefore provides sets of hybrid breeding indices for dairy cattle breeds or lines, that may differ depending on the partner breed or line to be utilized in the cross.

Those skilled in the art, reading the present disclosure, will appreciate that one feature and implication of inventive technologies is that breeding stock sires (or sire lines) and dams (or dam lines) are selected notwithstanding their own particular traits. That is, in accordance with the present invention, it is not necessary that a cow be a high milk producer herself to act as a dairy cow breed stock dam for one or more F1 cross-breed progeny as described herein. The present invention, therefore provides technologies that, exactly contrary to conventional wisdom, select and/or utilize as dairy cow individuals whose personal dairy production trait or traits may be profoundly sub-par (e.g., relative to breed norms, standards, indexes, etc.), and in particularly may be materially below that/those of its F1 cross-breed progeny.

Provided Herds

In some embodiments, the present invention provides for the creation and/or maintenance of high performing herds of cattle based upon desired traits. In some embodiments, herds can be generated through selection of F0 sires/sire lines and dams/dam lines as determined by the performance of hybrid cattle resulting from theses crosses. F0 cattle can be re-paired to generate new hybrid cattle with the desired traits. Techniques such as estrous synchronization and/or artificial insemination can aid the breeding of F0 cattle to more efficiently produce high performing hybrid cattle.

Alternatively or additionally, in some embodiments, herds of high performing hybrid cattle can be generated through embryonic manipulation. Gametes from F0 cattle can be collected and used to generate new hybrid cattle through in vitro fertilization and embryonic transfer. Gametes as well as fertilized embryos can be frozen and stored for later implantation to build up a herd of high performing hybrid cattle. In addition, sexed sperm can be used to favor the generation of females for replacement cattle or more milk producers within the herd.

Herds of cross-bred cattle can be produced from breeds of cattle including but not limited to: Holstein, Guernsey, Ayrshire, Red and White, Milking Shorthorn, Jersey, Brown Swiss, Norwegian Red, Belarus Red, Belted Galloway, Angus, Beefmaster, Black Hereford, Brahman, Brangus, Charolais, Florida Cracker, Hereford, Highland, Pineywoods, Red Angus, Santa Gertrudis, Simmental, Tajima, Texas Longhorn, Limosin, Wagyu, and any combination thereof.

Among other things, the present invention provides of hybrid cattle that are progeny of matings between F0 individuals where at least one of the F0 individuals was selected based on one or more attributes of prior hybrid progeny from matings involving gametes of the same F0 individual (or of another F0 individual in the same line, particularly on the dam side). The present invention also provides herds of such hybrid cattle, and also collections of F1 cross-breed embryos, which may be cryopreserved or otherwise prepared for storage, including for long term storage.

In some embodiments, provided hybrid herds are pregnant. In some embodiments, provided hybrid herds are pregnant with F1 hybrid embryos, e.g., that may have resulted from the same cross as that which generated the pregnant hybrid progeny, and/or from a repeat cross of the same F0 individuals (or individuals from the same line). In some embodiments, provided hybrid herds are pregnant with hybrid embryos from a second mating cross of the same breeds utilized in the first cross that generated the pregnant hybrid, wherein the second mating cross is considered to be an improved cross relative to the first cross because one or both of the F0 individuals whose gametes were utilized in the second cross was selected via a process of continued hybrid performance monitoring as described herein. In some embodiments, provided F1 herds have excess gestational capacity as compared with that required to maintain the herd; in some embodiments, some or all of the excess capacity is utilized to gestate beef cattle.

Embryonic and Fertilization Technologies

Various techniques have been developed and refined to permit humans to control and/or effect animal matings optionally without animal intercourse (e.g., natural service) or even animal contact. Representative such techniques include, for example, in vitro fertilization, artificial insemination, cryopreservation (freezing) of gametes or embryos, induction of multiple ovulations, embryo transfer, sex determination of sperm or embryos, nuclear transfer, cloning, etc.

In vitro production of ruminant embryos is a three-step process involving oocyte maturation, oocyte fertilization, and in vitro culture. Only 30-40% of such oocytes reach the blastocyst stage, at which they can be transferred to a recipient or frozen for future use. The quality of the oocyte can dramatically impact the proportion of immature oocytes that form blastocysts while the post-fertilization culture environment has a major influence on the quality of the blastocyst. In some embodiments, use of sperm of a specific gender in conjunction with in vitro embryo production is a potentially efficient means of obtaining offspring of the desired sex. Concerns regarding the use of sexed semen technology include the apparent lower fertility of sorted sperm, the lower survival of sorted sperm after cryopreservation and the reduced number of sperm that could be separated in a specified time period. Assessment of embryo quality is a challenge. Morphological assessment is at present the most popular method for embryo selection prior to transfer. Other non-invasive assessment methods include the timing of the first cleavage division which has been linked to developmental ability. Quantitative examination of gene expression is an additional valuable tool to assess the viability of cultured embryos. A substantial amount of evidence exists to demonstrate that the culture conditions to which the embryo is exposed, particularly in the post-fertilization period, can have perturbing effects on the pattern of gene expression in the embryo with potentially important long-term consequences.

IVF is a technique in which the oocytes are extracted from a donor cow by a method of aspiration from the reproductive tract. Selected oocytes are then incubated for a period of 24 hours; this is call the maturation period. After maturation, the eggs are fertilized 18 to 22 hours after the co-culture has been made. The embryos stay in the medium until the 7th day, when they are ready to be transferred. This technique has three main advantages over conventional In Vivo embryo collection. With IVF, it is not necessary to superovulate the cows, nor is it necessary to synchronize them. This is a major breakthrough since the donor cows are not exposed to hormones that might compromise the reproductive soundness of the animals, and they can be worked without prior preparation time for the procedure. Embryo production averages about 30% of the oocytes harvested, although this quantity varies depending on the breed, the donor cow, and also the mating. Another advantage with the IVF is that the animals can be aspirated every 20 days instead of every 60 as in In Vivo embryo collection. The other advantage of IVF is that the animals can be harvested at a very young age; this will create a major impact on breeding selection since it reduces the generation interval for the animals with a specific desirable trait.

Artificial insemination (AI) has been used to obtain offspring from genetically superior males for more than 200 years. Well known methods to cryopreserve (freeze) and store semen have made AI accessible to more livestock producers. In the same manner as cryopreservation of semen, embryo freezing allowed for the global commercialization of animals with high genetic qualities. Semen from bulls is especially amenable to freezing and long-term storage. In the dairy industry, where large numbers of dairy cows are managed intensely, AI is simple, economical, and successful. More than 60 percent of dairy cows in the United States are bred by AI. However, the situation is different for beef cattle, where breeding populations are usually maintained on range or pasture conditions. In the United States beef industry, AI accounts for less than 5 percent of inseminations.

Development of ET technology allows producers to obtain multiple progeny from genetically superior females. Fertilized embryos can be recovered from females (also called embryo donors) of superior genetic merit by surgical or nonsurgical techniques. The genetically superior embryos are then transferred to females (also called embryo recipients) of lesser genetic merit. In cattle, efficient techniques can recover fertilized embryos without surgery, but only one or sometimes two embryos are produced during each normal reproductive cycle. To increase the number of embryos that can be recovered from genetically superior females, the embryo donor is treated with a hormone regimen to induce multiple ovulations, or superovulation.

The beef industry in the United States prefers male calves, which tend to have higher body weights and higher feed efficiency (compared to female or heifer calves) when placed in feedlots for the growing and finishing stages of meat production. In contrast, the dairy industry prefers heifer calves, which will ultimately produce offspring and milk for human consumption. Thus, methods are needed to determine the sex of sperm or embryos so producers can control the sex of the offspring of their livestock.

Since the mid-1980s, technology has been developed to transfer the nucleus from either a blastomere (cells from early, and presumably undifferentiated cleavage stage embryos) or a somatic cell (fibroblast, skin, heart, nerve, or other body cell) to an enucleated oocyte (unfertilized female egg cell with the nucleus removed). This "nuclear transfer" produces multiple copies of animals that are themselves nearly identical copies of other animals (transgenic animals, genetically superior animals, or animals that produce high quantities of milk or have some other desirable trait, etc.). This process is also referred to as cloning. To date, somatic cell nuclear transfer has been used to clone cattle, sheep, pigs, goats, horses, mules, cats, rabbits, rats, and mice.

The technique involves culturing somatic cells from an appropriate tissue (fibroblasts) from the animal to be cloned. Nuclei from the cultured somatic cells are then microinjected into an enucleated oocyte obtained from another individual of the same or a closely related species. Through a process that is not yet understood, the nucleus from the somatic cell is reprogrammed to a pattern of gene expression suitable for directing normal development of the embryo. After further culture and development in vitro, the embryos are transferred to a recipient female and ultimately result in the birth of live offspring. The success rate for propagating animals by nuclear transfer is often less than 10 percent and depends on many factors, including the species, source of the recipient ova, cell type of the donor nuclei, treatment of donor cells prior to nuclear transfer, the techniques used for nuclear transfer, etc.

The present disclosure demonstrates the effectiveness of combining fertilization technologies with trait selection to improve performance in dairy cattle. The present disclosure appreciates that engineered mating technologies such as in vitro fertilization, artificial insemination, cryopreservation (freezing) of gametes or embryos, induction of multiple ovulations, embryo transfer, sex determination of sperm or embryos, nuclear transfer, cloning, etc. have not heretofore been extensively utilized for the production of dairy cattle. Without wishing to be bound by any particular theory, the present inventors propose that conventional wisdom has been that such techniques would not offer significant benefit in the dairy cattle industry, at least not of a nature or type that could justify their significant expense. The present disclosure demonstrates, however, that such technologies can offer significant, heretofore unappreciated benefits in the dairy cattle industry. For example, the present disclosure establishes that such technologies uniquely facilitate development, maintenance, surveillance, and/or improvement of F1 crossbreed dairy cattle herds.

In some embodiments, embryos generated as a result of F0 selection based upon hybrid performance can be supplied to other farms and businesses, for example to permit them to generate hybrid progeny and/or herds. In some embodiments, the present invention allows for a business method of screening hybrid cattle and recreating high-performing hybrid cattle by selective breeding using the F0 gametes of their parents.

EXEMPLIFICATION

Example 1

Reproducing Additional Hybrid Cattle Based on an Individual High Performing F1 Bovine The present Example demonstrates, among other things, the optimization of performance traits of cattle by selecting F0 sires/sire lines and dam/dam lines based upon the performance of hybrids.

Hybrid dairy cattle resulting from breeding programs are screened for various performance traits. Screening involves advanced genetic-based testing as well as simple observation and analysis of each bovine's milk output and other performance traits. Those that have the best milk production, fertility, resistance to disease, and overall health are recorded along with their ancestral lineage. Gametes from the F0 sires and dams that produced the high performing F1 bovine are collected and stored for generation of additional high performing F1 cattle. If they are available, the F0 males and females themselves are used for further breeding. Female calves that have reached sexual maturity are implanted with a pre-fertilized embryo (generated from the gametes of the ideal F0 sire and dam). To bias a pregnancy towards an either female or male offspring, spermatozoa are sexed. High-performing hybrid cattle are implanted with embryos from their F0 parents to help produce additional high performing sister and/or brother cattle as well as continue the milk production process.

Example 2

Creating a Herd of High-Performing Hybrid Cattle

Once high performing hybrid and their sires/sire lines and dams/dam lines have been established, a herd of high performing cattle will be created. The novel F1 cattle are screened and analyzed as in Example 1 to determine which are high performers. The F0 gametes from the parents of these new high performers are also used for subsequent F1 cattle production.

REFERENCES

1. Madalena et al. Evaluation of Strategies for crossbreeding of dairy cattle in Brazil. J. Dairy Sci. 73 (7), 1887-1901 (1990).
2. Schefers, J. M. and Weigel K. A. Genomic selection in dairy cattle: Integration of DNA testing into breeding programs. Animal Front. 2 (1), 4-9 (2012).
3. Xue et al. Milk production and energy efficiency of Holstein and Jersey-Holstein crossbred dairy cows offered diets containing grass silage. J. Dairy Sci. 94 (3), 1455-1464 (2011).

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:
1. A method of maintaining an F1 hybrid crossbreed herd of dairy cattle comprising steps of:
implanting an F1 hybrid crossbreed embryo into each of a plurality of F1 female dairy cattle, wherein each of the F1 female dairy cattle resulted from a first F1-selected crossbreed cross, wherein an F1-selected cross is one that involves fertilization of an F0 female gamete with an F0 male gamete, wherein the F0 male and female gametes are from different breeds; and
one or both of the F0 male and female gametes is from an F0 individual or line selected based on one or more improved performance characteristics of prior F1 progeny generated in crosses of the same individual or line;
wherein each implanted F1 hybrid crossbreed embryo results from a second F1-selected crossbreed cross.
2. The method of claim 1, wherein the second F1-selected crossbreed cross utilizes male F0 gametes from the same individual utilized in the first F1-selected crossbreed cross.
3. The method of claim 1, wherein the second F1-selected crossbreed cross utilizes a male gamete from an individual or line different from that utilized in the first F1-selected crossbreed cross.
4. The method of claim 3, wherein the different individual is selected based on improved performance of its F1 progeny relative to those of the corresponding F0 individual used in the first F1-progeny selected crossbreed cross.
5. The method of claim 4, further comprising steps of:
assaying one or more performance characteristics of a plurality of F1 individuals resulting from a plurality of crosses that utilize F0 gametes from one or both of the F0 individuals or lines utilized in the first F1-selected crossbreed cross;
comparing the assayed one or more performance characteristics with those of F1 individuals resulting from a plurality of crosses that utilize F0 gametes from the different F0 individual or line; and
selecting a different individual or line for a breeding stock individual or line.
6. The method of claim 1, wherein the second F1-selected crossbreed cross utilizes male F0 gametes and female F0 gametes from the same individuals utilized in the first F1-selected crossbreed cross.
7. The method of claim 1, wherein the second F1-selected crossbreed cross utilizes male F0 gametes from the same line utilized in the first F1-selected crossbreed cross.
8. The method of claim 1, wherein the second F1-selected crossbreed cross utilizes female F0 gametes from the same line utilized in the first F1-selected crossbreed cross.

9. The method of claim 1, wherein the second F1-selected crossbreed cross utilizes female F0 gametes from the same individual utilized in the first FI-selected crossbreed cross.

10. The method of claim 1, wherein the second F1-selected crossbreed cross utilizes female gametes from an individual or line different from that utilized in the first F1-selected crossbreed cross.

11. The method of claim 3, wherein the different line is selected based on improved performance of its F1 progeny relative to those of the corresponding F0 line used in the first F1 progeny selected crossbreed cross.

12. The method of claim 1, further comprising preparing said hybrid crossbreed embryo by in vitro fertilization and culture.

13. The method of claim 1, further comprising preparing said hybrid crossbreed embryo by in vivo fertilization and collection.

14. The method of claim 1, wherein said implanted hybrid crossbreed embryo is a previously frozen embryo.

15. The method of claim 1, wherein said F1 hybrid cross-breed embryo is a cross-breed embryo selected from the group consisting of a Holstein/Norwegian Red hybrid, a Holstein/Jersey hybrid, a Jersey/Norwegian Red hybrid, a Friesian/Danish Red hybrid, a Brown Swiss/Ayrshire hybrid, a Guernsey/Ayrshire hybrid, a Milking Shorthorn/Ayrshire hybrid, a Brown Swiss/Guernsey hybrid, a Guernsey/Milking Shorthorn hybrid, and a Milking Shorthorn/Brown Swiss hybrid.

16. The method of claim 1, wherein said F1 hybrid cross-breed embryo is an embryo of a Brahman F0 parent.

17. The method of claim 1, wherein said performance characteristics comprise: milk production, longevity, semen production, age at first calving, body depth, cell counts, cow conception rate, dairy form, daughter calving ease, daughter pregnancy rate, daughter still birth, fat pounds, fat percent, feet and legs score, fertility, final score, foot angle, fore udder attachment, front teat placement, heifer conception rate, ketosis, lameness rate and/or degree, locomotion, milk productive life, milking speed, protein percent, protein pounds, rear legs rear view, rear legs side view, rear teat placement, rear udder height, reproductive life, resistance to cold, resistance to disease, rump angle, rump width, somatic cell score, sire calving ease, sire still bilih, size, stature, strength, teat length, udder cleft, udder conformation, and udder depth.

18. The method of claim 1, wherein the F0 female gamete or the F0 male gamete is of a dairy cattle breed selected from the group consisting of Holstein, Friesian, Norwegian Red, Danish Red, Brown Swiss, Guernsey, Ayrshire, Jersey, Red & White, Milking Shorthorn, Lineback, Dutch Belted, Burlina, Belarus Red, Canadienne, Carora, Danish Jersey, Frankeston Red, German Black Pied, Brahman, Illawarra, and Meuse-Rhine-Issel.

19. The method of claim 1, wherein the performance characteristic for selection is not shared by F0 individuals.

20. The method of claim 1, wherein the performance characteristic for selection is superior in F1 as compared with both F0 parents or F0 lines.

* * * * *